(12) United States Patent
Pierce et al.

(10) Patent No.: US 12,702,805 B2
(45) **Date of Patent: *Aug. 11, 2026**

(54) METHODS AND DEVICES TO PREVENT PREMATURE BIRTH

(71) Applicant: Nine Medical, Inc., San Francisco, CA (US)

(72) Inventors: Ryan Kendall Pierce, Carl Junction, MO (US); Benjamin Kahn Cline, Palo Alto, CA (US)

(73) Assignee: Nine Medical, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/025,834

(22) Filed: Jan. 16, 2025

(65) Prior Publication Data

US 2025/0152926 A1 May 15, 2025

Related U.S. Application Data

(63) Continuation of application No. 18/478,290, filed on Sep. 29, 2023, now Pat. No. 12,233,228, which is a (Continued)

(51) Int. Cl.
*A61M 31/00* (2006.01)
*A61M 11/00* (2006.01)
*B05B 11/00* (2023.01)

(52) U.S. Cl.
CPC .......... *A61M 31/00* (2013.01); *A61M 11/007* (2014.02); *B05B 11/00* (2013.01); (Continued)

(58) Field of Classification Search
CPC ................ A61M 31/00; A61M 11/007; A61M 2205/3331; A61M 2210/14; A61M 2210/1475; A61M 31/002; B05B 11/00; A61F 5/0093; A61F 6/065; A61F 6/225; A61F 6/146; A61F 6/18; A61F 6/08; A61K 9/0036; A61B 10/0291; A61B 2017/1205
See application file for complete search history.

(56) References Cited

U.S. PATENT DOCUMENTS

| | | | |
|---|---|---|---|
| RE20,061 | E | 8/1936 | Kirk |
| 2,146,472 | A | 2/1939 | Heintz et al. |

(Continued)

FOREIGN PATENT DOCUMENTS

| | | | |
|---|---|---|---|
| CN | 2785605 | Y | 6/2006 |
| CN | 2917679 | Y | 7/2007 |

(Continued)

OTHER PUBLICATIONS

Becher et al.; The cervical mucus plug: Structured review of the literature; Acta Obstetricia et Gynecologica; 88(5); pp. 502-513; May 2009.

(Continued)

*Primary Examiner* — Ophelia A Hawthorne
(74) *Attorney, Agent, or Firm* — Shay Glenn LLP

(57) ABSTRACT

Methods and devices to affect types, proportion, quantity, distribution, or proliferation of microorganisms within a female reproductive system.

20 Claims, 10 Drawing Sheets

Related U.S. Application Data continuation of application No. 16/986,098, filed on Aug. 5, 2020, now Pat. No. 11,819,648, which is a continuation of application No. 15/707,982, filed on Sep. 18, 2017, now Pat. No. 10,773,062, which is a continuation of application No. 15/332,906, filed on Oct. 24, 2016, now Pat. No. 9,764,120, which is a continuation of application No. 14/992,914, filed on Jan. 11, 2016, now Pat. No. 9,474,885.

(60) Provisional application No. 62/102,018, filed on Jan. 10, 2015, provisional application No. 62/116,568, filed on Feb. 16, 2015, provisional application No. 62/181,208, filed on Jun. 18, 2015, provisional application No. 62/194,798, filed on Jul. 20, 2015.

(52) U.S. Cl.
CPC . *A61M 2205/3331* (2013.01); *A61M 2210/14* (2013.01); *A61M 2210/1475* (2013.01)

(56) References Cited

U.S. PATENT DOCUMENTS 2,616,421 A 11/1952 Greenberg
2,841,146 A 7/1958 Heuboski
3,107,671 A * 10/1963 Farina ................ A61M 3/0279 604/150
4,322,463 A 3/1982 Goepp et al.
4,381,771 A 5/1983 Gabbay
4,589,880 A 5/1986 Duhn et al.
4,770,167 A 9/1988 Kaali et al.
5,042,503 A 8/1991 Torok et al.
5,123,424 A 6/1992 Koch
5,301,680 A 4/1994 Rosenberg
5,510,064 A 4/1996 Koch
5,637,877 A 6/1997 Sinofsky
5,980,804 A 11/1999 Koch
6,134,466 A 10/2000 Rosenberg
6,254,537 B1 7/2001 Nguyen
6,350,463 B1 2/2002 Herman et al.
6,375,970 B1 4/2002 Bieniarz
6,526,980 B1 3/2003 Tracy et al.
6,589,216 B1 7/2003 Abbott et al.
7,763,059 B2 7/2010 Perez
8,408,212 B2 4/2013 O'Brien et al.
8,679,013 B2 3/2014 Ziarno et al.
9,474,885 B2 10/2016 Cline et al.
9,764,120 B2 9/2017 Cline et al.
10,773,062 B2 9/2020 Cline et al.
11,819,648 B2 11/2023 Cline et al.
12,233,228 B2 2/2025 Pierce et al.
2002/0193670 A1 12/2002 Garfield et al.
2003/0088217 A1 5/2003 Bergeron et al.
2003/0212382 A1 11/2003 Abbott et al.
2007/0255184 A1 11/2007 Shennib
2007/0261699 A1 11/2007 Callister et al.
2008/0082024 A1 4/2008 Meyer et al.
2009/0076340 A1 3/2009 Libbus et al.
2010/0331739 A1 12/2010 Maltz et al.
2011/0237972 A1 9/2011 Garfield et al.
2012/0035508 A1 2/2012 Van Leer
2012/0265090 A1 10/2012 Fink et al.
2013/0053657 A1 2/2013 Ziarno et al.
2013/0197324 A1 8/2013 Waterhouse et al.
2013/0211384 A1 8/2013 Raspagliesi
2013/0281861 A1 10/2013 Flomerfelt et al.
2014/0135587 A1 5/2014 Hess
2014/0180169 A1 6/2014 Peters et al.
2014/0210640 A1 7/2014 Rahman et al.
2014/0278229 A1 9/2014 Hong et al.
2016/0120435 A1 5/2016 Young
2016/0157717 A1 6/2016 Gaster
2016/0262649 A1 9/2016 Hayes-Gill et al.
2016/0331299 A1 11/2016 Cline et al.
2018/0296156 A1 10/2018 Penders et al.
2020/0146614 A1 5/2020 Cline et al.
2022/0125621 A1 4/2022 Pierce et al.
2022/0287624 A1 9/2022 Cline et al.

FOREIGN PATENT DOCUMENTS

CN 201783070 U 4/2011
JP S5812657 A 1/1983
JP 2002512180 A 4/2002
JP 2002515069 A 5/2002
JP 2003520071 A 7/2003
JP 2007508907 A 4/2007
JP 2012165787 A 9/2012
JP 2014116754 A 6/2014
WO WO00/06022 A1 2/2000
WO WO2001/021116 A1 3/2001
WO WO2007/130958 A2 11/2007
WO WO2012/129304 A2 9/2012

OTHER PUBLICATIONS

Firth-Cozens; Interventions to improve physicians' well-being and patient care; Social Science and Medicine; 52(2); pp. 215-222; Jan. 2001.

Graczyk et al.; Analysis of abdominal electrical activity of uterus-approximate entropy appoarch; IEEE, 22nd Annual EMBS International Conference, Chicago, IL; pp. 1352-1355; Jul. 23-28, 2000.

Heard et al.; Silk-based injectable biomaterial as an alternative to cervical cerclage: An in vitro study; Reproductive Sciences; 20(8); pp. 929-936; Aug. 2013.

Saling et al.; Role of operative early total cervix occlusion for prevention of late abortion and early prematurity; Proc. Of the 5th World Congress of Perinatal Medicine; Barcelona, Spain; pp. 602-607; Sep. 23, 2001.

Sciscione et al.; Intracervical fibrin sealants: A potential treatment for early preterm permature rupture of the membranes; Am J Obstet Gynecol; 184(3); pp. 368-373; Feb. 2001.

Cline et al.; U.S. Appl. No. 19/022,831 entitled "Devices and methods for monitoring pregnancy," filed Jan. 15, 2025.

* cited by examiner

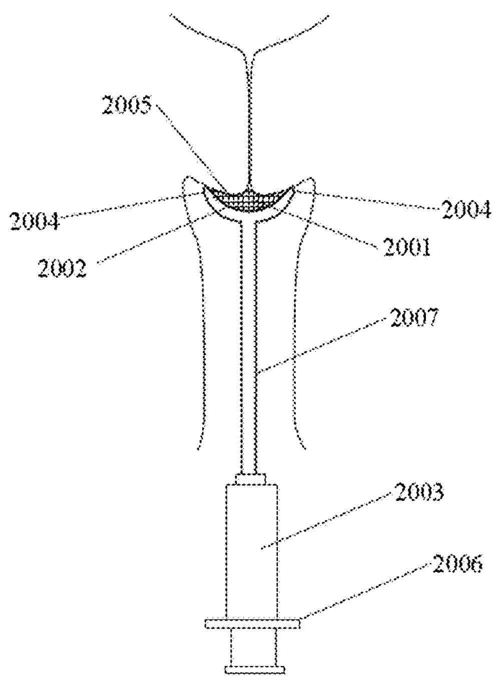
FIG. 20
2105
2104
2103
2102
2100
2101
FIG. 21
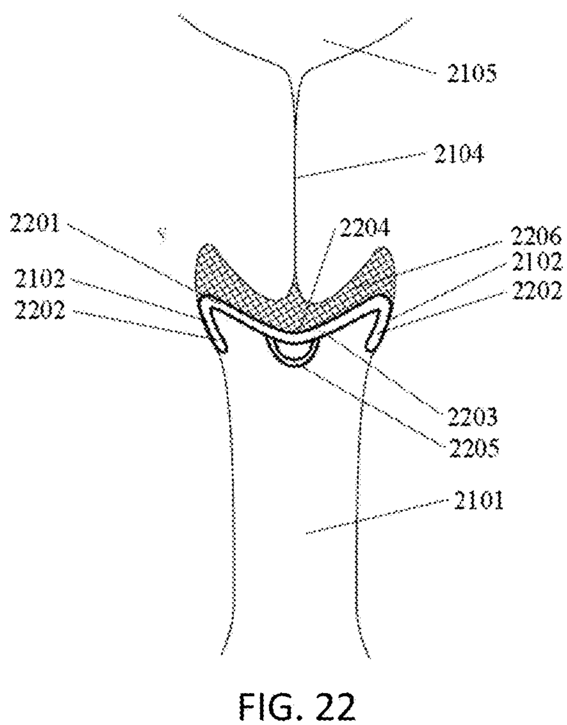
FIG. 22
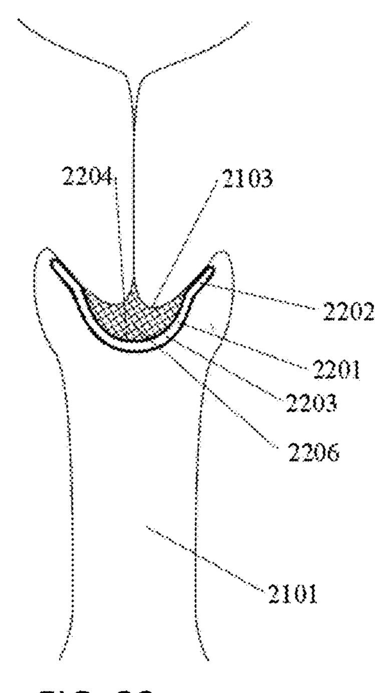
FIG. 23

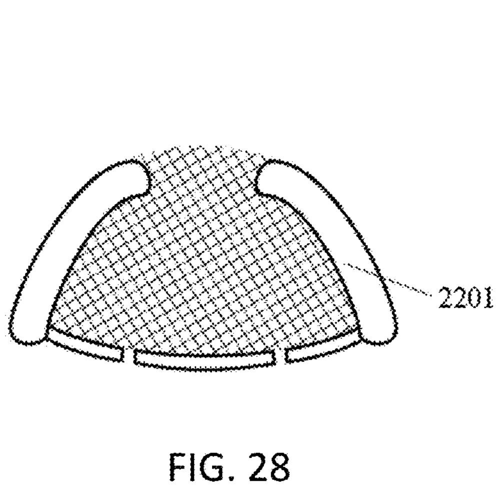
FIG. 28
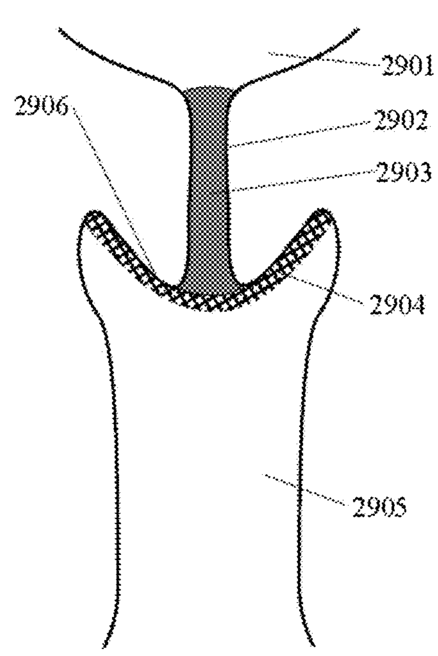
FIG. 29
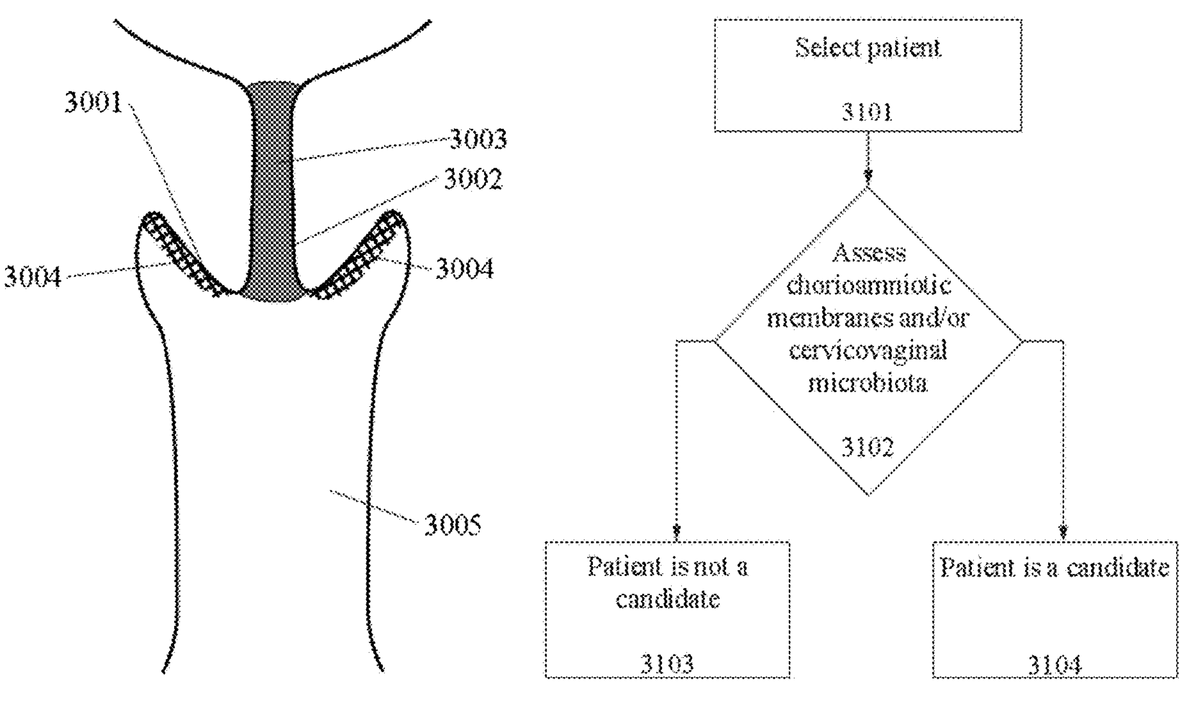
FIG. 30
FIG. 31

METHODS AND DEVICES TO PREVENT PREMATURE BIRTH

CROSS REFERENCE TO RELATED APPLICATIONS

This patent application is a continuation of U.S. patent application Ser. No. 18/478,290, filed Sep. 29, 2023, titled "METHODS AND DEVICES TO PREVENT PREMATURE BIRTH," now U.S. Patent Application Publication No. 2024/0100311, which is a continuation of U.S. patent application Ser. No. 16/986,098, filed Aug. 5, 2020, titled "METHODS AND DEVICES TO PREVENT PREMATURE BIRTH," now U.S. Pat. No. 11,819,648, which is a continuation of U.S. patent application Ser. No. 15/707,982, filed Sep. 18, 2017, titled "METHODS AND DEVICES TO PREVENT PREMATURE BIRTH," now U.S. Pat. No. 10,773,062, which is a continuation of U.S. patent application Ser. No. 15/332,906, filed Oct. 24, 2016, titled "METHODS AND DEVICES TO PREVENT PREMATURE BIRTH," now U.S. Pat. No. 9,764,120, which is a continuation of U.S. patent application Ser. No. 14/992,914, filed on Jan. 11, 2016, titled "METHODS AND DEVICES TO PREVENT PREMATURE BIRTH," now U.S. Pat. No. 9,474,885, which claims priority to U.S. Provisional Patent Application No. 62/102,018, filed on Jan. 10, 2015, titled "METHODS AND DEVICES FOR TRANSFER OF MICROBIOTA TO A FEMALE REPRODUCTIVE SYSTEM"; U.S. Provisional Patent Application No. 62/116,568, filed on Feb. 16, 2015, titled "METHODS AND DEVICES TO PREVENT PREMATURE BIRTH"; U.S. Provisional Patent Application No. 62/181,208, filed on Jun. 18, 2015, titled "METHODS AND DEVICES TO PREVENT PREMATURE BIRTH;" and U.S. Provisional Patent Application No. 62/194,798, filed on Jul. 20, 2015, titled "METHODS AND DEVICES TO PREVENT PREMATURE BIRTH," each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The methods and apparatuses described herein generally relate to the prevention of preterm birth by preventing or treating the undesirable proliferation of microorganisms within a female reproductive system. For example, described herein are methods and apparatuses for forming a protective barrier preventing the proliferation of microorganisms within a reproductive system.

BACKGROUND

Premature birth is a leading cause of neonatal morbidity and mortality, and can adversely affect health well into adulthood. While the causes of premature birth are inadequately understood, intra-amniotic infection is blamed in a significant proportion of cases. Microorganisms migrating and/or proliferating from or through the vagina and/or cervical canal may eventually invade the amniotic cavity, and can cause the release of cytokines, which fight infection but cause inflammation, which releases prostaglandins. These, in turn, may cause biochemical processes that lead to contractions and cervical dilation and in turn, premature birth. Therefore, it would be useful to provide methods and apparatuses (e.g. devices, systems, compositions and the like) that minimize or prevent the unwanted microorganisms in the amniotic cavity, which may help prevent premature birth.

Existing techniques for preventing premature birth and/or for reducing migration of unwanted microorganisms into the uterus are difficult to use, may not provide sufficient protection, and/or may lead to undesirable complications and side effects. For example, mechanical barriers, including inserts and sealants, have been proposed for insertion into the uterine cavity, or near the internal os, to reduce the risk of pre-term birth. See, e.g., U.S. Pat. Nos. 6,350,463, 6,375,970, and 8,408,212. However, such barriers and methods typically require insertion though the cervix and into the uterus, replacing or disrupting the cervical mucus plug. Further, these methods are both too invasive, and somewhat indiscriminate in the treated regions. What is needed are methods and apparatuses that may reduce or prevent the risk of migration of microorganisms into the cervical canal, but without disrupting the canal and cervical mucus plug. Described herein are method and apparatuses that may address this need.

SUMMARY OF THE DISCLOSURE

In general, described herein are methods and apparatuses for preventing preterm birth. In particular, described herein are intravaginal approaches and apparatuses for performing them, to prevent infection-related preterm birth. Any of the methods and apparatuses described herein may be configured to create a microbial barrier at the ectocervix (e.g., over or around the external os) of a woman's cervix without disrupting the cervical canal, and in particular, without disrupting a mucus plug within the canal.

For example, described herein are methods of applying a microbial barrier to an ectocervix of a cervix, and in particular, methods of applying a microbial barrier to an ectocervix of a cervix of a patient without disrupting a cervical mucus plug. These methods may include: inserting an applicator device through a vagina so that an applicator is adjacent the ectocervix; and forming the microbial barrier by applying a coating material over the ectocervix while preventing the coating material from contacting a vaginal wall and projecting into a cervical canal and disrupting the cervical mucus plug.

A method of applying a microbial barrier to an ectocervix of a cervix without disrupting a cervical mucus plug may include: confirming that a patient does not have a cervicovaginal infection; inserting an applicator device through the vagina so that a cup-shaped applicator is over the ectocervix; and forming the microbial barrier by applying a coating material over the ectocervix while preventing the coating material from contacting a vaginal wall and projecting into a cervical canal and disrupting the cervical mucus plug.

Any of these methods may include a step of limiting the pressure, flow rate or pressure and flow rate of the applied coating material from the applicator device to prevent disrupting the cervical mucus plug. Flow rate and/or pressure may be limited in any appropriate manner, as described herein. For example the applicator apparatus may include a flow sensor and/or pressure and feedback to control applied (delivery) pressure. In some variations the applicator may include a distal deflector to deflect a stream of the coating material emitted by the apparatus so that it is applied only tangentially to the ectocervix, and particularly at or near the opening into the cervical canal, to prevent directly emitting coating material into the cervical canal. Alternatively or additionally, the method may include applying the coating material at an angle relative to the tissue, so that when emitted by the applicator, the coating material is emitted against a diffusing or deflecting surface that then allows the coating material to contact the ectocervix with less force than the application force. Alternatively or additionally, the applicator may include a baffle at the distal end region of the applicator to reduce and/or limit the force and/or pressure of the coating material as it is applied. For example, a baffle may be a deflecting surface, as just mentioned, or it may be a sponge or porous member providing an indirect pathway between an aperture through the applicator and the ectocervix. Thus, in any of the methods described herein, the coating material may be applied via an indirect path from the aperture of the applicator to the surface of the ectocervix.

Any of the methods described herein may include a step of confirming that the vagina does not include an infection prior to forming the microbial barrier. For example, the method may include confirming that the patient does not have a cervicovaginal infection. Alternatively or additionally any of these methods may also include confirming that the patient does not have a disrupted chorioamniotic membrane prior to forming the microbial barrier.

Any of these methods described herein may include visualizing the cervix when applying the coating material, and in particular, visualizing the cervix (e.g., ectocervix of the cervix) through the applicator device. Thus, the applicator or a portion (e.g., the distal end of the applicator) may be transparent; alternatively or additionally the applicator may include a visualizing means such as a fiber optic, camera, or the like, near the distal end to visualize the ectocervix of the cervix before or while the apparatus is applying the coating material.

Any of these methods may also include removing overflow coating material back into the applicator device. As will be described in greater detail below, these apparatuses may include an overflow return path (e.g., channel) into which excess coating material may be removed, e.g., by an applied vacuum.

In general, applying the coating may include applying the coating from a cup-shaped end of the applicator device through one or more apertures on an inner surface of the cup-shaped end. As mentioned, the apertures and applicator may be configured so that the coating material is not applied directly into the cervical canal. For example, the one or more apertures may be located off-center relative to the inner surface, to prevent application of coating material directly into a cervical canal. The cup-shaped portion of the applicator is generally shaped and adapted to fit on the cervix in a predetermined manner. For example, the applicator distal end may include sidewalls or other portions that center it on the ectocervix so that the central region of the inner surface of the cup is positioned opposite from the cervical opening into the cervical canal. By positioning the apertures outside of the central region of the inner surface of the applicator, the cervical opening may be protected from having coating material applied directly (and with the application pressure), so that it may receive only low-pressure, indirect application of material. This may prevent coating material from entering into the cervical canal any significant distance, and minimize the chance that the application of coating material by the applicator will disrupt or dislodge the mucus plug. In some variations, the central region does not include any apertures for application of coating material.

Alternatively or additionally to the radial offset of the delivery apertures from the cervical canal (by positioning them outside of the central region), the apertures may be oriented to prevent application by the apparatus of coating material directly from the aperture into the cervical canal. For example, the aperture(s) may be oriented in a direction that would be normal to (+/−45 degrees, +/−30 degrees, +/−25 degrees, +/−20 degrees, +/−15 degrees, etc.) the face of the cervical opening when the applicator is positioned over the cervix. The apertures may be oriented by having the opening of the aperture angled so that fluid ejected from the aperture applies force in a direction that points away from the cervical opening. In some variations, a deflector plate or structure (which may include one or more apertures behind it) is positioned over the central region that will be positioned opposite from the cervical opening; the deflector may prevent coating material from being applied with any substantial force (pressure) into the cervical opening.

Any appropriate thickness of coating material may be applied. For example, the coating material may be applied in a thickness of the between about 0.5 mm and 1 cm (e.g., between about 0.75 mm and 1 cm, between about 1 mm and 1 cm, between about 2 mm and 1 cm, between about 3 mm and 1 cm, between about 4 mm and 1 cm, etc.; greater than 0.5 mm, greater than 1 mm, greater than 2 mm, greater than 3 mm, greater than 4 mm, greater than 5 mm, less than 2 cm, less than 1.5 cm, less than 1 cm, less than 0.9 cm, less than 0.8 cm, less than 0.7 cm, less than 0.6 cm, less than 0.5 cm, or any range between these) of coating material.

The coating may be re-applied regularly, e.g., every week, every 1.5 weeks, every 2 weeks, every 3 weeks, every 4 weeks, every 5 weeks, every 6 weeks, every 7 weeks, every 8 weeks, etc. (e.g., between 1-8 weeks, between 1-7 weeks, between 1-6 weeks, between 1.5-8 weeks, between 1.5-7 weeks, between 1.5-6 weeks, between 2-8 weeks, between 2-7 weeks, between 2-6 weeks, etc.

The coating material may be applied by the applicator in any appropriate manner. The coating material may be liquid or it may be a vapor (e.g., an aerosol) when applied from out of the apertures of the applicator. For example, the coating material may be sprayed. Thus, the apertures may include a nozzle or micronozzels to atomize the coating material.

The general, the applicator device may be inserted through the vagina and the distal end may engage the external cervix. The applicator may include an adjustable (e.g., bendable, tiltable, etc.) head and/or neck region to allow the (e.g., cup-shaped) distal end to be oriented onto, and in some variations over, the cervix ectocervix. The applicator may mechanically isolate the ectocervix from the vagina using the applicator device. For example, the cup-shaped applicator may be positioned over the ectocervix so that the inner surface of the applicator is opposite from the external os; the walls of the cup-shaped applicator may contact the cervix so that it fits into the cavity/opening formed by the cup-shaped end.

Any of the methods described above may be performed apparatuses, including generally devices or systems. A system may include parts that operate together but are not necessarily attached or always engaged with each other.

For example, an apparatus (e.g. device) for delivering a microbial barrier to an ectocervix of a cervix may include: an elongate body comprising a first delivery lumen configured to carry a coating material; a proximal end region having a handle; an applicator at the distal end of the elongate body that is configured to be aligned over the ectocervix, the applicator comprising an inner surface having a central region configured to be positioned opposite an opening into a cervical canal on the ectocervix when the applicator is aligned over the ectocervix; and one or more delivery apertures through the inner surface positioned outside of the central region, wherein the one or more delivery apertures are configured to deliver coating material from the first lumen to the ectocervix.

The apparatuses described herein may be devices for delivering a microbial barrier to an ectocervix of a cervix without disrupting a cervical mucus plug within a cervical canal. For example, the device may include: an elongate body comprising a first delivery lumen; a proximal end region having a handle and a chamber for a coating material wherein the chamber is continuous with the first delivery lumen; a cup-shaped applicator at the distal end of the elongate body that is configured to fit over the ectocervix and apply the coating material on the ectocervix but not into the cervical canal, the cup-shaped applicator comprising an inner surface having a central region configured to be positioned opposite an opening into the cervical canal when the cup-shaped applicator is over the ectocervix; and one or more delivery apertures through the inner surface, wherein the delivery apertures are outside of the central region or are oriented to prevent emitting coating material perpendicular to the central region and into the cervical canal when the cup-shaped applicator is over the ectocervix.

Any of the devices for delivering a microbial barrier to an ectocervix of a cervix without disrupting a cervical mucus plug within a cervical canal may include: a curved or bent elongate body comprising a first delivery lumen; a proximal end region having a handle and a chamber for a coating material wherein the chamber is continuous with the first delivery lumen; a cup-shaped applicator at the distal end of the elongate body that is configured to fit over the ectocervix and apply the coating material on the ectocervix but not into the cervical canal, the cup-shaped applicator comprising an inner surface having a central region configured to be positioned opposite an opening into a cervical canal on the ectocervix when the cup-shaped applicator is over the ectocervix; a plurality of delivery apertures through the inner surface positioned outside of the central region, wherein the delivery apertures are configured to deliver coating material from the first lumen to the ectocervix without disrupting a cervical mucus plug within the cervical canal.

In general, the apparatuses (e.g., devices) for delivering a microbial barrier are configured to apply, attach, seal, secure or otherwise connect a microbial barrier to the cervix, and specifically over the ectocervix of the cervix, including or surrounding the external os. As mentioned above, delivering may include spraying, ejecting, painting, or applying the coating material to form the microbial barrier. The barrier may cover the cervical opening, or it may surround the cervical opening. The barrier may be antimicrobial, e.g., containing an antimicrobial agent that may be embedded on or within the barrier, such as an antibiotic. An antimicrobial may therefore be released in a highly localized and controlled manner. The applied barrier may extend slightly into the cervix, but is typically excluded from the majority of the cervical canal. FIG. 1 illustrates a schematic of the anatomy, showing a vagina and the ectocervix of the cervix 101 with the central cervical opening 103 into the cervical canal 105. The external orifice of the uterus (or ectocervix) is a small, depressed, somewhat circular region on the rounded extremity of the vaginal portion of the cervix. As used herein, the ectocervix may include all of the vaginal-facing portion of the cervix up to the intersection with the walls of the vagina (the vaginal fornix). Thus, the ectocervix may include the external os. The ectocervix is the vaginal portion of the cervix, which typically has a convex, elliptical shape and projects into the cervix between the anterior and posterior vaginal fornices. On the rounded part of the ectocervix is a small, depressed external opening, connecting the cervix with the vagina. The size and shape of the ectocervix and the external opening (external os) can vary according to age, hormonal state, and whether natural or normal childbirth has taken place. In women who have not had a vaginal delivery, the external opening is small and circular, and in women who have had a vaginal delivery, it is slit-like. On average, the ectocervix is 3 cm (1.2 in) long and 2.5 cm (1 in) wide. Any of the apparatuses (e.g., the cup-shaped distal end) may be configured and adapted to at least partially enclose the ectocervix.

As mentioned, in any of the methods and apparatuses described herein, an antibacterial agent may be incorporated into the occlusive element. For example, one or more of the following antibacterial agents may be incorporated: chlorhexidine, chlorhexidine-silver sulfadiazine, chlorhexidine gluconate, chlorhexidine digluconate, or other chlorhexidine-based or chlorhexidine-containing agents; silver, silver diamine fluoride, silver-zinc zeolite, silver-ion, or other silver-based, silver-ion-based, or silver-containing agents; Acidulated phosphate fluoride, sodium fluoride, stannous fluoride, amine fluoride, ammonium hexafluorosilicate, ammonium hexafluorosilicate combined with cetylpiridinium chloride, or other fluorine-based or fluorine-containing agents; one of or a combination of zinc oxide, hydrated zinc sulfate, calcium sulfate hydrous, diatomaceous earth, dibutyl phthalate copolymer, and polyvinyl chloride; zinc-based or zinc-containing agents; rifampicin-miconazole, minocycline rifampicin, or fluconazole.

Where an occlusive structure (occlusive element) is inserted, it may include a material or a combination of materials having antibacterial properties. For example, one or more of the following materials or combinations of materials having antibacterial properties may be used: chitin, chitosan, dextran, hyaluronic acid, chondroitin sulfate, or a mixture of polydextran aldehyde and polyethylenimine.

In general, the coating material forming the microbial barrier is excluded from the cervical canal, and in the methods described herein may be excluded or prevented from being applied substantially into the cervical canal. Substantially excluded or prevented from being applied within the cervical canal means that the coating may be limited to (typically passive) application over less than 20% of the length of the cervical canal (e.g., less than 15%, less than 10%, less than 5%, etc.) typically from the vaginal side. Ideally, none of the cervical canal would be coated, but in some women, the cervical canal is relatively cone-shaped, so the coating material may enter a short distance into the cervical canal as the coating bridges the cervical opening (which it may do without disrupting the cervical mucus plug).

The microbial barrier may be formed of an occlusive material. Examples of occlusive materials, and properties of occlusive materials, are described in greater detail herein.

In general, the methods and apparatuses described herein may be adapted to prevent disruption of the cervical mucus plug. The cervical mucus plug, or operculum, is a plug that fills and seals the cervical canal during pregnancy. The plug is the natural barrier to prevent infection, but it may have additional benefits. Disrupting the plug may refer to dislodging (e.g., moving, unsealing, etc.), damaging (e.g., cutting, tearing, etc.), or the like. In some variations, the method and apparatuses described herein are configured so that they do not contact the cervical mucus plug (e.g., or the region of cervical canal where the plug normally resides) or minimally contact (e.g., just the proximal, vaginal-facing side) the mucus plug.

As mentioned, any of the apparatuses described herein may include a distal end that is cup-shaped. The cup-shaped distal end typically includes a cavity into which the ectocervix may fit. The cup-shape may be concave or it may be cylindrical or another shape. The cup-shape may have a circular mouth, or it may be oval. The cup-shaped distal end region typically includes one or more apertures for delivering the coating material from out of the applicator apparatus onto the ectocervix. The cup-shaped distal end may be hinged or jointed to allow adjustment of the positon of the cup-shaped distal end relative to the more proximal end of the elongate body. For example, the cup-shaped distal end may be attached via a bendable joint to allow the distal end to bend and/or rotate relative to the elongate body of the device. One or more steering mechanisms (e.g., tendons, wires, etc.) may be used to control bending (e.g., bend or prevent bending).

In general, the apertures may be openings through the inner surface, connecting to a delivery lumen carrying coating material (e.g., from a chamber that communicates with a proximal end of the device, such as the handle). The apertures may be oriented relative to the inner surface, so that the material ejected from the aperture will be directed primarily (having a principle force vector) at an angle relative to the inner surface (rather than simply perpendicular to the portion of the inner surface where the aperture is located. Any of the apertures described herein may include a nozzle or tip for shaping, forming, or directing the flow of coating material out of the apparatus.

Where multiple apertures are included, the different apertures may be different. For example, the delivery paths associated with at least two different delivery apertures may vary in length, diameter, or fluid resistance, such that at some stage or stages during application of the coating material, the cumulative volumes of coating material ejected from the at least two different delivery apertures are different. Staging the ejection of the material between the at least two different delivery apertures may result in a desired progression of delivery of the material to the ectocervix. In some embodiments, the desired progression may prevent air or bodily fluids from becoming trapped by the material.

Similarly or additionally, the apparatus may include two or more lumen (e.g., channels, passages, etc.) extending down the length of the elongate body of the apparatus from the proximal end to the distal end. Continuities between the chamber holding a coating material at the proximal end of the apparatus and two or more delivery lumens continuous with delivery apertures may be staged such that injected coating material reaches the continuities non-simultaneously (at different times). This staging may promote a desired progression of delivery of the material to an ectocervix. In some embodiments, the progression prevents air or bodily fluids from becoming trapped by the material.

Any of the apertures through the inner surface of the cup-shaped applicator may be recessed relative to the inner surface, resulting in a reduced pressure of injected coating material before the material enters a volume proximate the tissue targeted for coating. In some embodiments, coating material is progressively delivered to the ectocervix, beginning at central region of the inner surface of the cup-shaped applicator (typically corresponding to a site on the cervix spanning the opening to the cervical canal) and progressing to sites further from the central region (e.g., corresponding to the opening to the cervical canal). This progression may prevent trapping of air near the opening to the cervical canal. As mentioned above, the coating material may be applied indirectly or tangentially (e.g., at an angle relative to the cervical canal opening) to prevent driving the coating material into the cervical canal.

Alternatively or additionally, the one or more delivery aperture(s) may be positioned at a site nearer an opening to a cervical canal and a coating material may be delivered to the site before it is delivered to sites farther from the opening, to prevent air from becoming trapped at the site nearer the opening.

Any of these devices may also include an overflow channel on or through the applicator. The overflow channel may be continuous with a second lumen (e.g., a return lumen) through the elongate body. Additionally or alternatively, any of the apparatuses described herein may include an air escape lumen. For example, an air escape lumen may be positioned at a site near the opening to a cervical canal as coating material is applied, and removed after the coating material reaches the opening of the air escape lumen, to prevent air from becoming trapped during application of the coating material. The air escape lumen may be a structural part of the apparatus.

As mentioned above, any of the variations described herein may include a baffle configured to reduce the fluid pressure of the coating material ejected from the one or more delivery apertures. The baffle may be, for example, a deflector, a deflection plate and/or a sponge-like baffle on or within the inner surface of the applicator that is configured to reduce the fluid pressure of the coating material ejected from the one or more delivery apertures.

The one or more delivery apertures may be a plurality of delivery apertures arranged around the central region of the inner surface; this arrangement may prevent ejection of coating material through the one or more delivery apertures into a cervical canal.

In general, the elongate body may extend between a proximal end (e.g., handle) and the distal applicator tip (e.g., cup-shaped applicator). The elongate body maybe between 4 and 24 inches (e.g., between 4-18 inches, between 5-15 inches, etc.). The elongate body may be straight or it may be bent or bendable.

The applicator (e.g., cup-shaped applicator) may be attached to the elongate body with an adjustable neck region that is configured to allow adjustment of the angle of the cup-shaped applicator relative to the elongate body. In general, the applicator (e.g., cup-shaped applicator) at the distal end may include have gaps or channels that are configured to allow air to escape when the cup-shaped applicator is over (and/or on) the ectocervix.

Any of the apparatuses described herein may include a pressure limiter configured to limit the pressure of the coating material applied through the one or more delivery apertures. The pressure limiter may be active (e.g., pressure regulator) or passive.

Further, any of these apparatuses may be configured or adapted to allow imaging before, during or after application of the coating material. For example, any of these apparatuses may be configured so that the applicator is transparent, e.g., over at least a portion of the applicator to allow visualization of the ectocervix therethrough.

It should be understood that the inventions, embodiments, characteristics, and purposes described herein (including those described separately in Sections I and II) might be used in combination with one another. In a non-limiting example, devices and methods used to remove a substantially pre-shaped device placed within the female reproductive system may also be used to remove a material that assumes its shape substantially after placement. In another non-limiting example, devices and methods used to isolate one region of a female reproductive system from another region of the female reproductive system may also be used to deliver a therapeutic agent.

Although many of the variations described herein describe the application of a coating material, any of the variations may also be used with an implant such as a scaffolding and/or occlusive implant in addition to the occlusive coating material. For example, an occlusive material may be delivered on or around a scaffolding or reinforcing structure (material), or the scaffolding or reinforcing material is applied to the occlusive material after it is delivered. In addition, in some variations, a 'new' coating material layer may be applied over an existing or 'old' coating layer.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 1 illustrates the anatomy associated with the human female reproductive system as referred to herein.

FIG. 2 is another example of the anatomy of the uterus, vagina and cervical canal, showing an occlusive implant inserted into the vaginal canal. As described in detail herein, such implants may be included with the ectocervical barriers (e.g., coatings); alternatively the ectocervical barriers may be a preferred embodiment to such implants, preventing disturbance of the cervical canal and a mucus plug.

FIGS. 3, 4, 5, 6, 7, 8, 9, 10 and 11 each illustrate examples of barrier implants (occlusive implants or elements) that may be used.

FIG. 20 shows one example of an applicator apparatus (a device for delivering a microbial barrier to an ectocervix of a cervix) inserted within the anatomy of a patient, in which the coating material has been applied to the ectocervix.

FIG. 21 is another example, similar to FIG. 1, of the anatomy of a portion of a vagina, cervix and uterus.

FIG. 22 illustrates one example of a microbial barrier coating applied to an ectocervix with an implant structure that may be removed after forming the coating or left in place.

FIG. 23 illustrates another example of a microbial barrier coating applied to an ectocervix with an implant structure that may be removed after forming the coating or left in place.

FIG. 28 is an example of one variation of an implant device.

FIG. 29 is an example of an occlusive barrier (coating) covering an ectocervix and spanning the opening into the cervical canal.

FIG. 30 is another example of an occlusive barrier (coating) covering an ectocervix but not spanning the opening into the cervical canal.

FIG. 31 schematically illustrates one example of a method of selecting a patient for any of the treatments described herein (e.g., forming a microbial barrier).

DETAILED DESCRIPTION

Figures 12, 13, 14, 15:
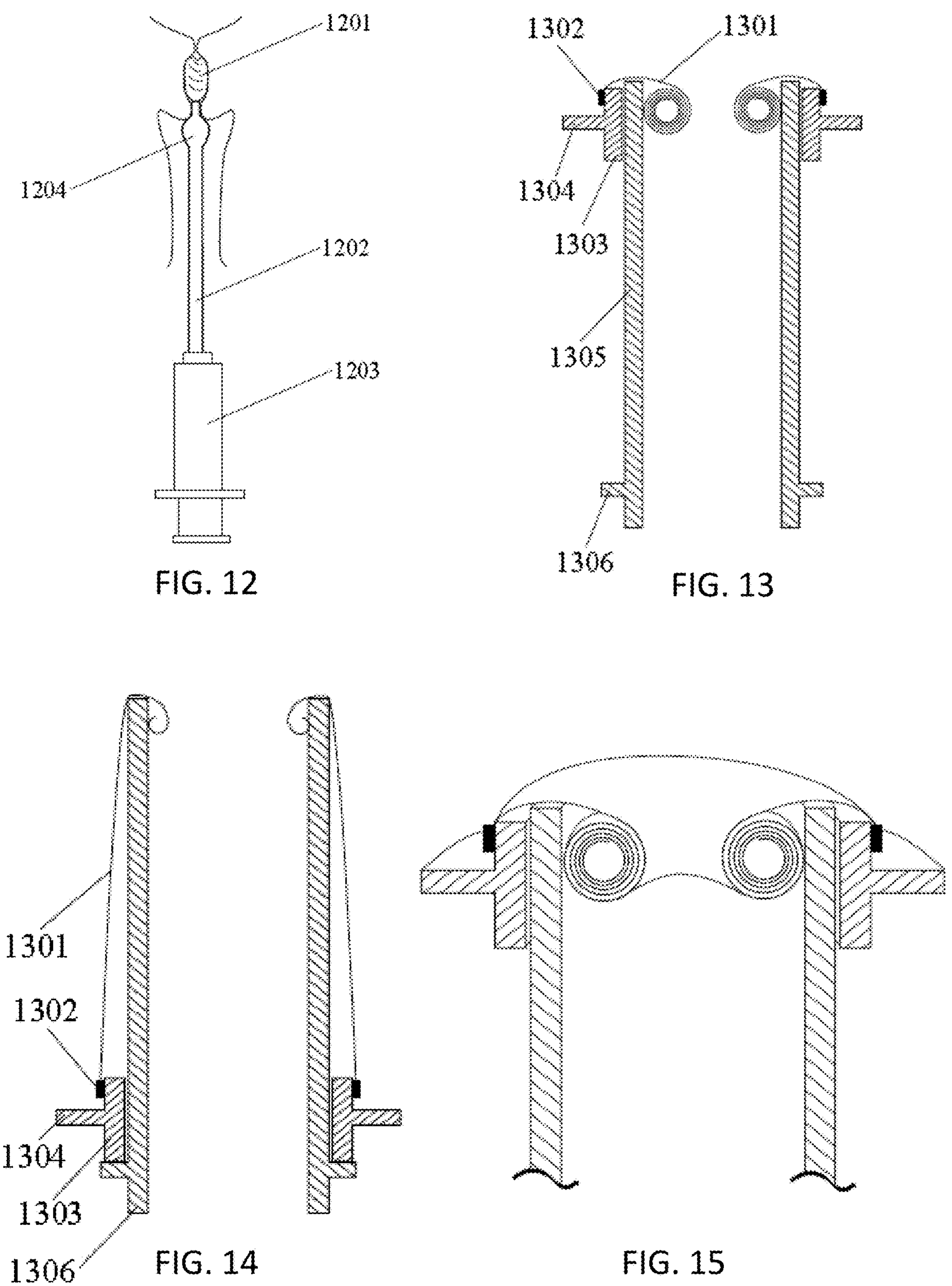
FIG. 12 illustrates one example of an insertion tool for a barrier implant that may be used to insert an occlusive implant into the cervical canal.
FIG. 13 shows one example of a tool for inserting and/or positioning a delivery sheath which may be used with any of the variations described herein.
FIG. 14 shows the apparatus of FIG. 13 with the sheath extended.
FIG. 15 shows a section through another example of a tool for inserting and/or positioning a delivery sheath which may be used with any of the variations described herein, similar to the one shown in FIGS. 13 and 14.

Described herein are methods and apparatuses for preventing pre-term birth by reducing or preventing the migration of microorganisms through the cervix using a microbial barrier. For example, the methods and apparatuses described herein may apply, insert, and/or deliver an occlusive element, which may be an occlusive member (structure) or an occlusive material which may form an occlusive member upon or shortly after delivery. In particular, described herein are methods an apparatuses for forming and/or applying a microbial barrier to an ectocervix of a cervix of a patient, without disrupting a cervical mucus plug, by delivering a coating material. The coating material typically forms the occlusive material (and may be referred to as such).

In general, the methods described herein may include inserting an applicator apparatus such as an applicator device, through the patient's vagina so that an applicator is adjacent the ectocervix and then forming the microbial barrier by applying a coating material over the ectocervix while preventing the coating material from contacting a vaginal wall and at the same time, preventing the coating material from projecting into a cervical canal and disrupting the cervical mucus plug.

In some embodiments, an occlusive element is positioned partly or fully within a vagina, cervical canal, and/or uterus, in order to isolate a first region where a first type, proportion, quantity, distribution, or proliferation of a microorganism is suspected to be or to become present, from a second region where the first type, proportion, quantity, distribution, or proliferation of the microorganism is unwanted. In some embodiments, the occlusive element is positioned in contact with a vagina, cervix, and/or uterus, in order to isolate a first region where a first type, proportion, quantity, distribution, or proliferation of a microorganism is suspected to be or to become present, from a second region where the first type, proportion, quantity, distribution, or proliferation of the microorganism is unwanted. The occlusive element may comprise a device, material, or combination thereof. In some embodiments, methods and devices prevent microbial invasion of amniotic cavity and/or intra-amniotic infection during pregnancy, which in some cases may lead to premature birth.

In some embodiments, the occlusive element is positioned partly or fully in a vagina, cervical canal, and/or uterus to interrupt the migration and/or proliferation (for example, by reproduction) of microorganisms from a first site proximal (herein defined as closer to the vaginal opening) to the occlusive element to a second site distal (herein defined as farther from the vaginal opening) to the occlusive element. In some embodiments, methods and devices prevent intra-amniotic infection during pregnancy, which in some cases may lead to premature birth.

In some embodiments, the occlusive element provides full or partial obstruction to a path of migration and/or proliferation of microorganisms.

Prospective patients may be screened to determine candidacy for an occlusive element therapy, wherein occlusive element therapy comprises delivery of the occlusive element to a vagina, cervix, and/or uterus of a patient. For example, the cervical mucus of a prospective patient may be sampled and assessed to determine candidacy for occlusive element therapy. In some cases, candidates for the occlusive element therapy may be chosen according to one or more of the following criteria: having previously given birth prematurely to a child; previous miscarriage; positive or negative test for a particular type, proportion, quantity, distribution, and/or proliferation of microorganisms in her reproductive system; elevated risk of premature birth, according to known and/or suspected risk factors; cervical insufficiency; prior cervical surgery; removal of at least a portion of a cervical gland; having a reproductive tract infection; having bacterial vaginosis; having intermediate bacterial flora as assessed based on a Nugent score; elevated vaginal pH; having an elevated level of sialidase in at least a part of her reproductive system; elevated cervical mucus permeability; elevated cervical mucus spinnbarkeit; cervical mucus elasticity; and low cervical mucus viscosity. In some cases, a prospective patient's cervicovaginal epithelial barrier may be assessed to determine candidacy for treatment with one or more embodiments described herein; epithelial barrier permeability may be assessed using fluorometry and/or impedance measurement.

In some cases, the occlusive element is comprised of a substantially pre-formed device. In some cases, the substantially pre-formed device assumes a volume inside the female reproductive system that is bounded at least in part by body tissues, and in some cases, body tissues impart pressure on the substantially pre-formed device that contributes to maintain the pre-formed device's position. In some cases, the structure of the substantially pre-formed device, its delivery system, and/or the nature of interaction between the substantially pre-formed device and body tissues bears similarity to that of a tampon, including resemblance to a shortened tampon. In some cases, the substantially pre-formed device is comprised of one or more of the following: soft components (for example, features that contact body tissues), for reasons that may include promoting conformance to body tissues (for example, to reduce microorganism proliferation pathways), minimizing trauma to body tissues, and/or achieving comfort; stiff components, which may provide structural support to the pre-formed device; components that offer some compliance (for example, for ease of insertion, and/or to flex to adapt to the general path of the female reproductive system). In some embodiments, the substantially pre-formed device comprises a stiff component (or component that offers some compliance), substantially surrounded by a soft component. In some embodiments, the substantially pre-formed device comprises a structure coated with a growth affecting agent (for example, an antibiotic). In some cases, the substantially pre-formed device is sponge-like.

In some embodiments, the substantially pre-formed device is configured to deliver therapy (for example, antibiotic therapy). In some cases, the substantially pre-formed device elutes a chemical or drug. In some cases, the substantially pre-formed device contains a reservoir of microorganisms (for example, a collection of microorganisms transplanted from a donor, or cultivated from a collection of microorganisms originally sourced in whole or part from a donor) and/or growth affecting agent. In some cases, the substantially pre-formed device delivers light (for example, ultraviolet light) to desirably affect microorganism growth, type, proportion, quantity, distribution, or proliferation, in some cases at particular and/or varying wavelengths, intensities, and/or durations. In some cases, the substantially pre-formed device provides or promotes temperature therapy (such as heat or cold). In some cases, the substantially pre-formed device contains one or more batteries (in some cases, one or more batteries that may be inductively charged). In some cases, the substantially pre-formed device features one or more of the following: a pH sensor, a temperature sensor, or a chemical sensor. In some cases, the substantially pre-formed device has data storage and/or data transmission (including wireless transmission) capabilities. In some cases, data may be transferred from the substantially pre-formed device after its removal from the female reproductive system, after which it may be discarded, replaced or reused. In some cases, the substantially pre-formed device captures a sample of the microorganism population, which may be evaluated to determine growth, type, proportion, quantity, distribution, or proliferation (or changes in these parameters) of microorganisms. In some cases, the substantially pre-formed device (or the gel, liquid, mixture, colloid, foam, solution, suspension, and/or other material described elsewhere) may change color in response to the types, proportion, quantity, distribution, or proliferation of microorganisms within the female reproductive system.

In some cases, the occlusive device comprises a gel, liquid, mixture, colloid, foam, solution, suspension, and/or other material which has a first viscosity (or hardness) before delivery to a site in the vagina, cervical canal, and/or uterus, and which assumes a second viscosity (or hardness) after delivery. In some cases, the first viscosity (or hardness) is lower than the second viscosity (or hardness). In some cases, the device or material assumes a shape of a volume bounded at least in part by the interior of the vagina, cervical canal, and/or uterus. In some cases, a transition of the viscosity or hardness of the device or material within the vagina, cervical canal, and/or uterus occurs without further action by a medical professional or the recipient of the device or material. In some cases, the transition is enabled and/or accelerated by one or more of the following: addition of one or more chemicals, exposure to light (for example, ultraviolet light), exposure to heat (for example, body heat), cooling, exposure to bodily fluids, and exposure to other fluids. In some cases, the first viscosity (or hardness) is greater than the second viscosity (or hardness), which in some cases facilitates handling during delivery as well as accommodation to surrounding anatomy after delivery.

In some cases, the gel, liquid, mixture, colloid, foam, solution, suspension, and/or other material comprises one or more of the following: a biocompatible polymer, keratin, cyanoacrylate, bismuth subnitrate (in some cases, in an oil base), bioresorbable materials, ethylene vinyl copolymer dissolved in dimethyl sulfoxide, poly (vinyl acetate-ethylene) copolymer clear thermoplastic, polyurethane, polyethylene, PTFE, clay, kaolinite, alginate, silk, and laminated thermoplastic. In some cases, two or more chemicals are mixed to prepare the gel, liquid, mixture, colloid, foam, solution, suspension, and/or other material shortly before clinical use, in order that the gel, liquid, mixture, colloid, foam, solution, suspension, and/or other material hardens at a desired time.

In some cases, the gel, liquid, mixture, colloid, foam, solution, suspension, and/or other material is treated to achieve transition from a first state to a second state, inserted into the vagina, cervical canal, and/or uterus, and allowed to transition to a third state. In some cases, the gel, liquid, mixture, colloid, foam, solution, suspension, and/or other material is softer in the first and third states than in the second; in some of these cases, the treatment is cooling. In some cases, the gel, liquid, mixture, colloid, foam, solution, suspension, and/or other material is harder in the first and third states than in the second; in some of these cases, the treatment is warmth. In some cases, the treatment is mechanical compression, and at least part of the gel, liquid, mixture, colloid, foam, solution, suspension, and/or other material behaves viscoelastically; in some of these cases, mechanical compression allows easier delivery into the vagina, cervical canal, uterus, and/or a delivery system. In some cases, the material used is a thermosoftening plastic.

For example, the coating materials described herein, which may be applied to form the occlusive structure (e.g., the microbial barrier) may be based on, derived from, or comprised of one or more of the following materials or material categories: albumin, albumin with aldehyde cross linker, bovine serum albumin, chitin, chitosan, chitosan-catechol, chitosan mixed with DOPA (L-3,4-dihydroxyphenylalanine), cyanoacrylate, n-butyl-2-cyanoacrylate, n-butyl-2 cyanoacrylate combined with methacryloxysulfolane, 2 octyl-cyanoacrylate and butyl lactoyl cyanoacrylate, 2-octyl-cyanoacrylate, fibrin, gelatin, gelatin-thrombin, gelatin-resorcinol-formaldehyde, gelatin-resorcinol-formaldehyde-glutaraldehyde, gelatin-poly(L-glutamic acid), glutaraldehyde-albumin, mussel-mimetic materials, marine adhesive protein, algae-mimetic materials, lysine, L-lysine, poly(acrylic acid), poly(glycerol sebacate), photocrosslinkable poly(glycerol sebacate) derivatives, poly(ethylene glycol), dopamine-functionalized poly(ethylene glycol), polysaccharide-based hydrogels, dextran, hyaluronic acid, chondroitin sulfate, polyester, polysine, ε-polylysine, urethane, poly(ethylene glycol) combined with trilysine amine and N-hydroxy succinimide, poly(ethylene glycol) combined with hydrogen chloride and sodium phosphate-sodium carbonate, poly(ethylene glycol) combined with trilysine amine, poly(ethylene glycol) combined with polysine and tyramine, tetra-succinimidyl poly(ethylene glycol) and trilysine amine, accrylated poly(ethylene glycol) combined with polyester primer and photoinitiator, glutaryl-succinimidyl ester combined with thiol terminated poly(ethylene glycol), fibrin glue combined with aprotinin, poly (L-lactic acid), polyvinyl alcohol, tyramine-modified polyvinyl alcohol, fibrinogen combined with thrombin, fibrinogen combined with a ruthenium photo-catalyst, bovine collagen combined with thrombin, gelatin and N-hydroxysuccinimide-ester functionalized poly(L-glutamic acid) or disuccinimidyl tartrate, photocrosslinkable gelatin adhesives, gelatin combined with microbial transglutaminase, bovine albumin and glutaraldehyde, human albumin and a NHS-activated poly(ethylene glycol), lactobionic acid and azide functionalized chitosan, tyrosine-modified chitosan combined with HPR and hydrogen peroxide, thiol-containing chitosan and maleimide containing ε-polylysine, aldehyde-containing dextran and amine-containing poly(ethylene glycol) or polylysine crosslinkers, aldehyde-bearing chondroitin sulfate and poly (vinyl alcohol-co-vinyl amine), methacrylate and aldehyde functionalized chondroitin sulfate, NHS-activated chondroitin sulfate and amine-containing poly(ethylene glycol), poly(L-glutamic acid).

The coating material used may be particular useful in the variations described herein in which the coating material is applied to the ectocervix to form the microbial barrier. In such applications, the coating material may be chosen or modified to have material properties (including viscosity, Young's Modulus, etc.) that are well-suited for this use, to prevent patient discomfort and extended use. For example, Albumin-based material may have a Young's modulus between about 1400-5000 KPa; Chitin-based or Chitosan-based material may be between about 0.5 KPa-6 GPa; Cyanoacrylate-based material may be between about 200-1200 MPa; Fibrin-based material may be between about 20-150 KPa; Gelatin-based material may be between about 5-75 KPa; Mussel-mimetic material may be between about 1500-4500 KPa; Poly(acrylic acid)-based material may be between about 20-40 Kpa; Poly(glycerol sebacate)-based material may be between about 50-1380 KPa; Polyethylene-glycol-based material may be between about 20-200 KPa In some cases, an injection device (which may include a syringe) may be temporarily inserted into the vagina, cervical canal, and/or uterus, and used to inject the gel, liquid, mixture, colloid, foam, solution, suspension, and/or other material.

In some embodiments, an injection device or other delivery device may track usage (for example, one or more of the following: the amount of occlusive material used, either cumulatively and/or in a single administration; the date, time, and/or frequency of usage; positioning of the device relative to the anatomy; speed of injection; whether or not the device was properly operated). In some embodiments, usage information may store and transmitted to a separate receiver, such as a phone. In some embodiments, received information may be processed, and/or displayed to the user of the device, a medical professional, and/or others. In some embodiments, a mobile phone application is used to recommend proper usage of the device, and/or provide additional guidance related to health and/or pregnancy.

In some cases, the gel, liquid, mixture, colloid, foam, solution, suspension, and/or other material is provided sterile.

In some cases, a patient may be oriented, with respect to the direction of the Earth's gravity, such that an injected or otherwise introduced gel, liquid, mixture, colloid, foam, solution, suspension, and/or other material will migrate in a desired direction, or will not migrate in an undesired direction. For example, a patient may be oriented such that injected or otherwise introduced gel, liquid, mixture, colloid, foam, solution, suspension, and/or other material will be gravitationally pulled proximally toward the vaginal opening.

In some cases, the gel, liquid, mixture, colloid, foam, solution, suspension, and/or other material partly or fully surrounds a component that provides structural support to the gel, fluid, or other material after hardening, or aids in removal of the gel, liquid, or other material. For example, the component may be a tether that is more easily reached or gripped by a removing person or instrument. In some cases, the component may act as a conduit for the gel, liquid, mixture, colloid, foam, solution, suspension, and/or other material as it is injected into the body; for example, it may feature one or more ports through which the gel, liquid, mixture, colloid, foam, solution, suspension, and/or other material exits the component into the body, and one or more ports through which the gel, liquid, mixture, colloid, foam, solution, suspension, and/or other material enters the conduit. A proximal portion of the conduit may be removed after injection of the gel, liquid, mixture, colloid, foam, solution, suspension, and/or other material.

In some cases, the occlusive element is delivered using a delivery system. The delivery system may be configured to facilitate delivery while minimizing the introduction of unwanted microorganisms into the female reproductive system, and/or configured to minimize the displacement of microorganisms from first proximal sites in the female reproductive system to second distal sites in the female reproductive system.

In some cases, the delivery system comprises a syringe with a pressure limiting feature. For example, the syringe may contain a pressure relief valve that may prevent sealant from being ejected from the syringe with an undesired pressure, velocity, and/or momentum. Limiting the pressure, velocity, and/or momentum of the sealant as it is ejected in the vicinity of an ectocervix may prevent the sealant from disturbing a cervical mucus plug, damaging an epithelium of a cervix, and/or transferring microbiota towards the cervical canal. The delivery system may further comprise an overflow volume in which sealant that is ejected from the syringe via the pressure limiting feature is constrained. For example, the overflow volume may prevent sealant ejected from the syringe via the pressure limiting feature from contacting a tissue of a patient.

In some cases, the delivery system comprises an automated dispensing system with a syringe, an actuator, and a switch. In some embodiments, the actuator is a linear actuator. An operator may press the switch, causing the actuator to drive a plunger of the syringe into a barrel, and thereby dispensing an occlusive element. In this way, the fluid flow parameters in dispensing the occlusive element may be decoupled from the actions of the operator. Additionally, the automated dispensing system may contain a pressure limiting feature. For example, the automated dispensing system may contain pressure sensor and a closed loop control system designed to prevent the pressure in the barrel of the syringe from exceeding a target value.

In some cases, the delivery system comprises a member with a negatively pressured lumen or chamber, which aspirates mucus and/or fluids (for example, bodily fluids or provided fluids) that might otherwise be displaced to more distal sites. The negatively pressured lumen or chamber may be connected to an at least partially external negative pressure source, such as a syringe (with which negative pressure may be manually provided, or provided using an energy-storing spring).

In some cases, the delivery system comprises a pressure relief feature and a delivery lumen. In some embodiments, the pressure relief feature is a lumen. In some embodiments the pressure relief feature is a channel on the outer surface of an elongate body. In some cases, when the distal tip of the delivery system is positioned near an external os of a cervix, sealant may be delivered to the ectocervix of the cervix via the delivery lumen, and air and/or bodily fluids may enter the pressure relief feature. The pressure relief feature may reduce the pressure in the vicinity of the external os of the cervix during delivery of the sealant.

In some embodiments, the delivery system comprises an aspiration lumen and a delivery lumen. An operator may utilize a delivery system to aspirate cervical mucus (for example, from the cervical canal), and then deliver part or all of an occlusion element to at least part of a volume previously occupied by the aspirated cervical mucus.

In some cases, the delivery system comprises a delivery sheath which advances into the vagina, cervical canal, and/or uterus, in a manner that minimizes or prevents a given portion of the delivery sheath that contacts a wall of the vagina, cervical canal, and/or uterus at a first proximal region of the wall from subsequently contacting a second, significantly more distal region of the wall. In some cases, advancing is executed by pressurizing the delivery sheath. For example, the delivery sheath may be coupled to syringe, wherein compression of the syringe pressurizes the delivery sheath with gas or liquid. The delivery sheath may comprise an everting structure, such as an everting balloon, that upon pressurization advances distally by everting, uneverting, unrolling, or unfurling. In some cases, a delivery lumen is coupled to the distal end of the advanced delivery sheath, such that an occlusive element may be delivered via the advanced delivery sheath.

In some cases, the delivery sheath is advanced using a force-transmitting feature that unrolls, unfurls, and/or uneverts the delivery sheath.

In some embodiments, after advancing the delivery sheath, an operator may deliver an occlusive element. For example, the operator may deliver an occlusive element comprising a fibrin adhesive to the ectocervix of the cervix. Delivery of the occlusive element may be achieved by manually compressing a syringe containing the occlusive element, wherein the syringe is coupled to a delivery lumen extending through a distal portion of the delivery sheath.

The delivery sheath may comprise one or more of the following: a vessel, a bladder, a bag, and a liner. In some embodiments, the delivery sheath, prior to pressurization, assumes a folded, rolled, everted, inverted, furled, and/or bunched configuration that may promote or allow generally distal migration during pressurization. In some cases, advancing is executed by advancing a structure within the delivery sheath. In some cases, the rate or extent of advancement is limited and/or controlled using a tether attached to delivery sheath (in some cases, to the inside of its distal end when advanced). In some cases, the rate or extent of advancement is limited and/or controlled by a restoring feature coupled to the delivery sheath. In some cases, after the delivery sheath is positioned within the female reproductive system, a component and/or material is positioned within the delivery sheath, which may cause the delivery sheath to expand radially to improve apposition with the wall of the vagina, cervical canal, and/or uterus. In some cases, the position of the component and/or material may be substantially maintained (as by pushing it in a distal direction) while a liner is removed; in some cases, the delivery sheath may remain positioned in the vagina, cervical canal, and/or uterus.

An operator may prepare a region of the female reproductive system for the occlusive element therapy by altering microbiota of the region. In some embodiments, preparing the region comprises rinsing the region with a saline solution. For example, an operator may insert an infusion catheter into the vagina of a patient, and advance the catheter until a distal end of the catheter nears the cervix. The operator may attach a saline-filled syringe to the catheter, and manually compress the syringe, thereby delivering saline to tissue surrounding the external os of the cervix. Rinsing the region may reduce the population of undesired bacteria in the region. The infusion catheter may then be used for delivery of the occlusive element. In some embodiments, the delivery system includes a device and/or a material utilized to prepare a region of the female reproductive system for the occlusive element therapy.

In some embodiments, preparing the region comprises delivering a fluid containing an anti-bacterial agent to the region. For example, an operator may deliver an aqueous solution containing povidone-iodine to the region. In some embodiments, preparing the region may comprise delivering a probiotic to the region.

In some embodiments, an operator utilizes devices and methods for altering microbiota of the region at least one of: prior to delivery of the occlusive element, during delivery of the occlusive element, and after delivery of the occlusive element.

In some embodiments, preparing the region comprises administering an antibiotic, probiotic, microbiota transfer, or another treatment to the recipient of the occlusive element therapy, in order to achieve a desired type, proportion, quantity, distribution, or proliferation of microorganisms in the recipient's reproductive system prior to placing the occlusive element therapy into the recipient's reproductive system.

Delivery of the occlusive element to a patient may be conducted with imaging, such as transcutaneous ultrasound. The delivery system for delivery of the occlusive element may contain a visualization feature. For example, a catheter for delivery of the occlusive element may contain an optical fiber coupled to a viewing system. The delivery system may contain a light source. For example, a catheter for delivery of the occlusive element may contain a light source coupled to a light guide, wherein light from the light guide is emitted at and/or near the distal end of the device.

In some embodiments, a camera, scope, and/or fiber optic is integrated into, or used in conjunction with, the occlusive element delivery system in order to enable proper positioning of the delivery system and/or occlusive element. In some embodiments, a light source is integrated into, or used in conjunction with, the occlusive element delivery system.

In some embodiments, direct visualization may be employed for delivery of the occlusive element. In some embodiments, a speculum may be utilized for delivery of the occlusive element. In some embodiments, the occlusive element may be delivered in a procedure utilizing a hysteroscope. For example, a catheter for delivery of the occlusive element may be advanced through the working channel of a hysteroscope prior to delivery of the occlusive element.

Any of the apparatuses described herein may be integrated with another apparatus such as a speculum, hysteroscope, or the like. For example, the device or a delivery system for the device may be coupled to a speculum. A delivery system coupled to a speculum can be advanced in a manner partially, but not fully, constrained by the coupling to the speculum; for example, the delivery system may be constrained to movement along the primary axis of insertion of the speculum, toward or away from the cervix, which in some embodiments may enable an operator to position a delivery aperture a desired distance from an ectocervix of a cervix for application of coating material.

In some embodiments, an occlusive element and/or a coating material may be formulated to be radiolucent on ultrasound imaging. In some embodiments, an occlusive element and/or a coating material may be formulated to be appear anechoic or hypoechoic on ultrasound imaging. In some embodiments, an occlusive element and/or a coating material may be formulated to facilitate ultrasound coupling and/or transmission.

In some embodiments, the delivery system comprises a catheter, wherein the catheter comprises an elongate body, a delivery lumen and a locating feature. For example, an operator may accurately position the catheter relative to an ectocervix of a cervix by advancing the catheter wherein the locating feature comprises a tapered and rounded tip, then placing the tip against an ectocervix of a cervix. The operator may deliver the occlusive element into the cervical canal from a syringe coupled to the catheter. In another example, wherein the locating feature comprises a tapered and rounded catheter tip, an operator may advance the tip of the catheter into the cervical canal and deliver the occlusive element from the catheter into the cervical canal.

In some embodiments, the locating feature may comprise a locating surface that surrounds at least a portion of the external surface of the cervix during a step in delivery of the occlusive element. For example, the locating surface may comprise a flexible concave member. In some embodiments, the locating surface may be fixed. In other embodiments, the locating surface may be expandable, for example comprising an expandable distal tip.

In some embodiments, the locating feature of the catheter may comprise an expandable distal tip. The operator may advance the catheter into the vagina with the expandable distal tip in a retracted position, for example wherein the distal tip has a substantially similar outer diameter to the outer diameter of a proximal portion of the catheter. The operator may then position the expandable distal tip in the vicinity of an external os of a cervix and may expand the expandable distal tip. The operator may position the expandable distal tip around a portion of the cervix. The operator may then deliver an occlusive element from a syringe coupled to the catheter via a delivery lumen to the external surface of the cervix. The distal ostium of the delivery lumen may be recessed from the distal end of the expandable distal tip.

In some embodiments, the delivery system comprises an elongate body and an insertion limiting feature. An insertion limiting feature may comprise a member located near a tip of the elongate body with a width greater than a width of a typical cervical canal during pregnancy. The insertion limiting feature may enable an operator to position the tip of the elongate body near an ectocervix of a cervix without accidentally disrupting the cervical mucus plug and/or the epithelium of the cervical canal. In some embodiments, the insertion limiting feature may prevent insertion of the delivery system into the cervical canal. In some embodiments, the insertion limiting feature may limit depth of insertion of the delivery system into the cervical canal to a predetermined depth. In some embodiments, the elongate body comprises an applicator tip that is coupled to a syringe.

In some embodiments, a light shone from an occlusive element delivery device onto cervicovaginal tissues indicates the zone, part of the zone, or approximately the zone onto or into which an occlusive element will be sprayed or otherwise applied. In some embodiments, the light is a laser light. In some embodiments, the light is an LED light. In some embodiments, the light pattern substantially forms a ring, interrupted ring, or other boundary-representing path surrounding the zone, part of the zone, or approximately the zone. In some embodiments, the light may be directed onto the opening of the cervical canal (e.g., the endocervix), or centered on the cervical canal, in order to properly aim the delivery of the occlusive element. In some embodiments, the focal length of the light may be set such that a desired distance between the delivery device and the targeted tissues is achieved when the light shone on the targeted tissues comes into focus.

In some embodiments, the delivery system comprises a syringe, a delivery lumen, and a shaping feature. For example, the occlusive element, which may comprise a gel, liquid, mixture, colloid, foam, solution, suspension, and/or other material, may be delivered from the syringe through the delivery lumen to the tissue surrounding the external os of the cervix, and confined spatially by the shaping feature during delivery. The shaping feature, which may comprise a concave surface surrounding a distal ostium of the delivery lumen, may spatially confine the occlusive element in a desired shape, thickness, and/or position while the occlusive element transitions in viscosity and/or hardness, for example, due to a chemical reaction. After the delivery system is removed, at least a portion of the occlusive element may comprise a shape formed with the shaping feature. The shaping feature may enable an operator to deliver an occlusive element with a uniform thickness.

The delivery system may contain one or more of the following: a soft distal tip, a bulb shaped tip, a flexible shaft, an echogenic tip, an echogenic shaft, a feature to mechanically prevent over-insertion, and markings along a shaft to facilitate determination of insertion depth.

In some cases, the occlusive element and/or one or more material to be used in forming the occlusive element, is prefilled in the delivery system before the delivery system and/or a portion thereof is positioned in a female reproductive tract.

In some embodiments, the occlusive element comprises a surgical adhesive and/or a surgical sealant. For example, the occlusive element may comprise one or more of the following: a fibrin sealant, a cyanoacrylate adhesive, a hydrogel, a polyethylene glycol polymer, and a gelatin-thrombin sealant. The occlusive element may comprise a material derived from one or more of the following: a fibrin sealant, a cyanoacrylate adhesive, a hydrogel, a polyethylene glycol polymer, and a gelatin-thrombin sealant. The occlusive element may be configured to dissolve, resorb from a patient's body, and/or be absorbed by a patient's body. The occlusive element may be configured to swell less than a predetermined threshold percentage in volume, and/or to swell more than a predetermined threshold percentage in volume. The occlusive element may be configured to adhere to the epithelium of a patient's female reproductive system.

In some embodiments, a target region of patient's female reproductive system that is intended for contact with the occlusive element is prepared prior to delivery of the occlusive element. For example, fluid may be removed from the target region, promoting improved adherence of the occlusive element, wherein the occlusive element comprises surgical sealant.

In some embodiments, the occlusive element may provide mechanical support to a patient's female reproductive system. For example, the occlusive element comprising a surgical sealant may provide mechanical support to a cervix of a patient with cervical insufficiency. In some embodiments, the occlusive element is utilized in conjunction with a mechanical support element for providing mechanical support to a patient's female reproductive system. For example, the occlusive element may be utilized in conjunction with a silicone cervical pessary.

In some embodiments, the occlusive element may be delivered as a spray from a distal end of the delivery system. In some embodiments, the occlusive element comprising a liquid and/or a gel may be ejected from a distal end of the delivery system. In some embodiments, pushing the plunger of a syringe may be advance and/or eject the occlusive element comprising a liquid and/or a gel. In some embodiments, a distal sheath of the delivery system may be retracted, exposing the occlusive element. In some embodiments, the occluding element comprising a liquid and/or a gel may be advanced and/or ejected by opening a valve between the occluding element and a pre-pressurized chamber.

In some embodiments, the occlusive element is composed of one or more of the following: a biocompatible polymer, keratin, cyanoacrylate, bismuth subnitrate (in some cases, in an oil base), bioresorbable materials, ethylene vinyl copolymer dissolved in dimethyl sulfoxide, poly (vinyl acetate-ethylene) copolymer clear thermoplastic, polyurethane, polyethylene, polytetrafluoroethylene, polypropylene, silicone, polysulfone, polyamide clay, kaolinite, alginate, and laminated thermoplastic.

In some embodiments, the occlusive element promotes conditions that change and/or maintain a type, proportion, quantity, distribution, or proliferation of microorganisms in the vagina, cervical canal, or uterus. For example, the occlusive element may include growth affecting materials, agents, or geometries (such as growth promoting agents, materials, or geometries, or growth retarding agents, materials, or geometries). In some cases, the growth affecting agents, materials, or geometries disproportionately and/or oppositely affect a first group of microorganisms, compared with other groups of microorganisms.

In some embodiments, after delivery of the occlusive element, an operator assesses efficacy of the occlusive element in providing occlusion. In some embodiments, a fluid-based assessment is utilized. For example, an operator may deliver a solution containing indocyanine green to a vagina of a patient, then use fluorescence imaging to determine whether the occlusive element provides a desired level of occlusion by assessing the relative level of fluoresce proximal and distal to the occlusive element. In another example, an operator may deliver an ultrasound contrast agent to a patient's vagina, then use ultrasound imaging to determine whether the occlusive element provides a desired level of occlusion.

In some embodiments, a non-fluid based assessment is utilized. For example, the occlusive element may comprise a fibrin sealant and a fluorescent compound. After delivery of the occlusive element, an operator may assess occlusion provided by the occlusive element by shining on the occlusive element a light that excites the fluorescent compound, inspecting light emitted by the fluorescent compound, and determining whether the occlusive element provides sufficient coverage of a target anatomy. In some embodiments, the occlusive element contains a colorant visible under white light illumination that aids in determining whether the occlusive element provides sufficient coverage of a target anatomy. For example, the occlusive element may contain a biocompatible blue colorant.

In some cases, the delivery system comprises a deformable vessel, bladder, bag, or liner, which is filled in part or whole with an occlusive element. In some cases, the deformable vessel, bladder, bag, or liner is delivered in a first step, and the occlusive element delivered in a second step. In some cases, the deformable vessel, bladder, bag, or liner is unfurled into the vagina, cervical canal, and/or uterus, in a manner that minimizes or prevents a given portion of the vessel, bladder, bag, or liner that contacts a wall of the vagina, cervical canal, and/or uterus at a first proximal region of the wall from subsequently contacting a second, significantly more distal region of the wall. In some cases, unfurling is executed by pressurizing the vessel, bladder, bag, or liner. In some cases, unfurling is executed by advancing a structure within the vessel, bladder, bag, or liner. In some cases, the rate or extent of unfurling is limited using a tether attached to the bag.

In some cases, the device, material, or combination thereof is provided sterile.

In some cases, a use in a woman of the occlusive element and/or the delivery system may begin at a first gestational age, and end at one or more of the following: achievement of a gestational age determined to represent a full-term pregnancy; achievement of a gestational age determined to surpass the range of gestational ages during which a premature birth can occur; achievement of a gestational age at which the invention's residual marginal benefits do not justify or require further use; childbirth; determination that the patient is of sufficiently low risk of amniotic infection causing premature birth; determination that the types, proportion, quantity, distribution, or proliferation of microorganisms in the woman's reproductive system do not, or no longer, require use of the invention; determination that the invention poses unacceptable risks to the woman or a fetus, or is response for unacceptable adverse effects on the woman or a fetus; and determination that biomarker-related criteria have been met.

In some cases, the use may begin before pregnancy, or outside of pregnancy, for example to achieve or preserve a desirable type, proportion, quantity, distribution, or proliferation of microorganisms. In some cases, the use may end upon achievement of the desirable type, proportion, quantity, distribution, or proliferation of microorganisms.

In some cases, the use may include at least one replacement of the occlusive element. In some cases, a replacement occlusive element may differ from that or those replaced, for example to adjust to changes in anatomy (for example, those associated with pregnancy), or in response to changing conditions in the female reproductive system (for example, the types, proportion, quantity, distribution, or proliferation of microorganisms within the woman's reproductive system).

In some embodiments, an operator may deliver a first occlusive element to a cervical canal of a patient. After a period of time has elapsed since the delivery of the first occlusive element, for example three weeks after the delivery of the first occlusive element, the operator may assess the first occlusive element, determine that a second occlusive element would be beneficial, and deliver the second occlusive element to the patient. In some embodiments, the operator may remove at least a part of the first occlusive element. In some embodiments, the first occlusive element may be retained in the patient. In some embodiments, the operator performing the delivery of the first occlusive element is different from the operator performing the delivery of the second occlusive element. In some embodiments, delivery of the second occlusive element may be required due to resorption, dissolution, and/or absorption of at least a portion of the first occlusive element.

In some embodiments, following delivery of the occlusive element to a pregnant patient, the patient may deliver a baby by vaginal birth. In some embodiments, at least a portion of the occlusive element may be altered and/or removed prior to birth of the baby. For example, an operator may form a lumen through the occlusive element prior to birth of the baby. In some embodiments, an operator may apply a solvent to the occlusive element prior to the birth of the baby. In some embodiments, at least a portion of the occlusive element may be altered by one or more of the following: peeling, cutting, dilating, and aspirating.

In some embodiments, a property of the occlusive element may be temperature sensitive. For example, viscosity of the occlusive element may increase with increasing temperature. An operator may apply a surface with a cold temperature to the occlusive element, reducing the viscosity of the occlusive element and enabling removal.

In some embodiments, altering and/or removing at least a portion of the occlusive element may happen without intervention of an operator. In some embodiments, the occlusive element may be absorbed and/or resorbed by a patient's body. For example, an occlusive element comprising a fibrin sealant may be absorbed by a patient's body.

In some cases, a removal-aiding component, such as a string, may extend from the occlusive element toward (and in some cases, out of) the vaginal opening. In some cases, a separate instrument may be used to engage with the occlusive element to facilitate removal. For example, a first removal-facilitating feature at or near the distal end of the separate instrument, and a second removal-facilitating feature at or near the proximal end of the occlusive element, may engage upon advancement of the separate instrument into the female reproductive system, enabling removal of the occlusive element upon removal of the separate instrument. In some cases, the first and second removal-facilitating features may be a first magnet and a second magnet.

In some embodiments, following delivery of the occlusive element to a pregnant patient, the patient may deliver a baby by Cesarean section. In some embodiments, the occlusive element is altered and/or removed after birth of a baby. In some embodiments, the occlusive element is altered and/or removed shortly before the birth of a baby.

The occlusive element may be tested after removal to gather information about the type, proportion, quantity, distribution, or proliferation of microorganisms in the woman's reproductive system. Removal may be performed in a manner that allows the occlusive element to be transferred to a storage container with minimized or no contamination (for example, from the remover's hands). For example, a storage container may feature a gripping feature or surface (for example, shaped like a bag or glove), that is contacted, in at least some locations, on one side by a removing person or instrument, but not on another side that contacts a component of the occlusive element that aids in removal.

In some embodiments, a vagina, cervical canal, and/or uterus is occluded by endoluminal coagulation, in order to isolate a first region where a first type, proportion, quantity, distribution, or proliferation of a microorganism is suspected to be or to become present, from a second region where the first type, proportion, quantity, distribution, or proliferation of the microorganism is unwanted.

In some embodiments, the occlusive element, substantially pre-formed device, gel, liquid, mixture, colloid, foam, solution, suspension, device, system, kit, and/or other material described herein, and/or the delivery tools described herein, can be self-applied or self-inserted by a pregnant woman.

In some embodiments, a kit may be provided that includes one or more applicators. Instructions may be provided that direct the pregnant woman to perform the application once, or a multitude of times at an instructed frequency, according to a provided calendar or schedule, or as the integrity of a previously applied occlusive element is deemed to have been at least partially compromised.

In some cases, a kit may be provided that comprises at least one occlusive element delivery system. In some cases, the kit may further comprise at least of the following: a speculum, an antiseptic, gloves, printed instructions, and gloves.

In some embodiments, applicators comprise an elongated device inserted into the vagina, from which a solution is sprayed or otherwise released from the leading end following an action performed by the operator (for example, the compression of a syringe contained within or connected to the elongated device). In some cases, the solution is pressurized by the operator or the operator's action, and expelled at the leading end. In some cases, the solution is pre-pressurized, and the operator's action causes a pathway to open and the solution to be released at the leading end.

In some embodiments, the solution resides at the leading end of the applicator, and upon insertion of the applicator into the vagina, assumes a position conducive to performing one or more of the invention's intended functions. For example, advancement of the applicator may position the solution around the ectocervix of the cervix. In some embodiments, both a solution and a containing device may be positioned by the applicator and left behind as the applicator is removed, with or without a release mechanism.

In some embodiments, applicators comprise an elongated device inserted into the vagina, from which a substantially preformed device is released. In some cases, the substantially pre-formed device contains a pressure sensitive adhesive that is released from the elongated device after contacting a target tissue.

In some embodiments, a substantially pre-formed device contains a feature to aid in the placement and/or re-positioning of the device. For example, the substantially pre-formed device may contain a handle.

In some embodiments, an applicator or delivery device is comprised of one or more of the following: a syringe, a soft material at least partially surrounding the syringe, a tip that desirably focuses or disperses the occlusive material.

The occlusive element, substantially pre-formed device, gel, liquid, mixture, colloid, foam, solution, suspension, device, system, kit, and/or other material described herein might perform one or more of several functions. In a first example function, it may occlude a path of ascension or proliferation of microorganisms from one location in the female reproductive system to another location (for example, from the vagina through the cervical canal to the amniotic cavity) and/or occlude a path or site of direct exposure between microorganisms and cervicovaginal tissues (for example, the external os of the cervix), which could lead to inflammation and/or cervical remodeling. In a second example function, it may make a tissue layer that it contacts, covers (directly or indirectly), or isolates less likely to absorb fluids containing microorganisms or microorganism-derived products (for example, preserving epithelial integrity and thereby protecting stromal tissue layers) and/or less likely to contact microorganisms or microorganism-derived products. In a third example function, it may structurally support a desired configuration, location, or position of anatomical features it contacts, or to which it imparts force or pressure (such as to prevent or mitigate cervical insufficiency, and/or to perform the function of a pessary). In a fourth example function, it may house components that detect environmental or anatomical changes (such as changes in a pregnancy-related state, such as cervical hardness or dimensions), or store or transmit information (such as information related to changes in a pregnancy-related state). In a fifth example, it may house components that contain and/or deliver therapy (such as heat, cold, medication, a chemical agent, a probiotic agents, or an antibiotic agent), in some embodiments in response to detected environmental or anatomical changes and/or changes in gestational age. Its varied descriptions and embodiments and associated delivery tools, delivery methods, patient selection protocols, and procedural applications described in this application should be understood to apply to embodiments featuring any combination or subset of these example functions. Moreover, these example functions should be understood to interact and in some cases, overlap.

In some embodiments, the occlusive element, substantially pre-formed device, gel, liquid, mixture, colloid, foam, solution, suspension, device, system, kit, and/or other material described herein leaves at least one path from the vagina into the cervical canal unobstructed. The at least one path left unobstructed may: allow the migration of nutrients, molecules, bodily fluids, or materials; enable examination of or access to the cervical canal or cervical mucus plug; and/or ease delivery of an infant. In some embodiments, obstruction of at least one path from the vagina into the cervical canal can be temporarily adjusted or suspended. For example, the occlusive element, substantially pre-formed device, gel, liquid, mixture, colloid, foam, solution, suspension, device, system, kit, and/or other material described herein may be positioned partly or fully within a vagina, cervical canal, and/or uterus, leaving at least one path from the vagina into the cervical canal unobstructed, while isolating a first region where a first type, proportion, quantity, distribution, or proliferation of a microorganism is suspected to be or to become present, from a second region where the first type, proportion, quantity, distribution, or proliferation of the microorganism is unwanted.

In some embodiments, the occlusive element, substantially pre-formed device, gel, liquid, mixture, colloid, foam, solution, suspension, device, system, kit, and/or other material described herein is configured to lengthen, rather than fully obstruct, a path of migration or proliferation of microorganisms from the vagina into the cervical canal, which may allow evacuation of bodily fluids or materials from the cervical canal. For example, it may block a first set of one or more migration or proliferation paths, but provide a second set of one or more continuous paths along surfaces at least partially created by it, while creating or preserving a path for evacuation of bodily fluids or materials from the cervical canal.

In some embodiments, the occlusive element, substantially pre-formed device, gel, liquid, mixture, colloid, foam, solution, suspension, device, system, kit, and/or other material described herein is applied to the ectocervix of the cervix, while a device shields a region overlapping with the opening of the cervical canal. For example, a feature of a device may rest on a region of the ectocervix of the cervix, covering the opening of the cervical canal while a solution is sprayed on or otherwise applied to the ectocervix of the cervix.

In some embodiments, the effective obstruction and/or permeability of the occlusive element, substantially pre-formed device, gel, liquid, mixture, colloid, foam, solution, suspension, device, system, kit, and/or other material described herein varies between sites. For example, the permeability at sites overlapping the opening into the cervical canal may be less than the permeability at sites covering or coating the ectocervix of the cervix, in order to allow migration of bodily fluids in and/or out of the cervical canal.

In some embodiments, the occlusive element, substantially pre-formed device, gel, liquid, mixture, colloid, foam, solution, suspension, device, system, kit, and/or other material described herein structurally supports a desired configuration, location, or position of anatomical features it contacts, or to which it imparts force or pressure (for example, such as to prevent or mitigate cervical insufficiency, and/or to perform the function of a pessary). It may be reinforced with structural elements that increase its hoop stiffness. The compressive force on the ectocervix of the cervix it provides by the occlusive element may be adjustable, for example by tightening filaments or bands that circumnavigate at least part of the ectocervix of the cervix.

In some embodiments, the occlusive element, substantially pre-formed device, gel, liquid, mixture, colloid, foam, solution, suspension, device, system, kit, and/or other material described herein is configured to indicate whether rupture of the membranes has occurred. For example, an occlusive element comprising a sealant may contain a chemical such as nitrazine that changes color based on pH. If the rupture of the membranes occurs, the color of the chemical may change due to exposure to amniotic fluid. In some embodiments, alpha-fetoprotein, creatinine, urea, and/or placental alpha-microglobulin 1 may be used as a marker for rupture of the membranes.

In some embodiments, the occlusive element, substantially pre-formed device, gel, liquid, mixture, colloid, foam, solution, suspension, device, system, kit, and/or other material described herein contains a sensor to detect a marker for rupture of the membranes and communication means to convey a notice of whether rupture of the membranes to a handheld device. For example, an occlusive element may contain a pH sensor coupled to signal processing means, a processor with an analog to digital convertor, and a Bluetooth module.

In some embodiments, the occlusive element, substantially pre-formed device, gel, liquid, mixture, colloid, foam, solution, suspension, device, system, kit, and/or other material described herein is configured to, following contact with amniotic fluid, degrade, detach, and/or otherwise allow the amniotic fluid to reach the vagina. For example, an occlusive element comprising a sealant may degrade upon exposure to a pH typical of amniotic fluid.

In some embodiments, the occlusive element, substantially pre-formed device, gel, liquid, mixture, colloid, foam, solution, suspension, device, system, kit, and/or other material described herein is configured to measure or monitor properties of the cervical tissue, cervical mucus plug, uterus, and/or cervicovaginal environment, that indicate a pregnancy-related state. For example, the occlusive element, substantially pre-formed device, gel, liquid, mixture, colloid, foam, solution, suspension, device, system, kit, and/or other material described herein may be configured to measure cervical tissue electrical impedance, cervical tissue fluorescence and/or uterine electrical activity. In some embodiments, information is stored, and in some embodiments, information is transmitted to a receiver (for example, a smart phone) and used for one or more of the following: to determine the need for reapplication or replacement of the occlusive element, substantially pre-formed device, gel, liquid, mixture, colloid, foam, solution, suspension, device, system, kit, and/or other material described herein; and/or to assess risk of preterm labor.

In some embodiments, the occlusive element, substantially pre-formed device, gel, liquid, mixture, colloid, foam, solution, suspension, device, system, kit, and/or other material described herein transmits information that can be used to assess its level of function and/or need for replacement. For example, the exposure of an embedded element to the cervicovaginal environment, correlating to the resorption or degradation of the embedding material, may change the effective resistance of a circuit that is included the embedded element. Said change in resistance may trigger transmission of information that may be used to determine the need for reapplication or replacement of the occlusive element, substantially pre-formed device, gel, liquid, mixture, colloid, foam, solution, suspension, device, system, kit, and/or other material described herein; or to assess risk of preterm labor.

In some embodiments, the cervical mucus plug naturally formed in the cervical canal of a pregnant woman is evaluated, and based on the evaluation, a treatment decision is made.

The evaluation may be based on one or more characteristics of the cervical mucus plug, such as: length, permeability, impedance, modulus of elasticity, spinnbarkeit, storage modulus, loss modulus, transparency, and/or color. Characteristics may be determined using ultrasound, optical analysis, direct visualization, application of an electric current, application of a chemical agent, or other means. Characterization may be performed in vivo, or part of the cervical mucus plug may be removed and evaluated in situ.

If the cervical mucus plug is deemed to be inadequate to provide satisfactory protection against ascending infection, a decision may be made to treat the pregnant woman with the invention.

Figures 1, 2, 3, 4, 5, 6, 7, 8, 9, 10, 11:
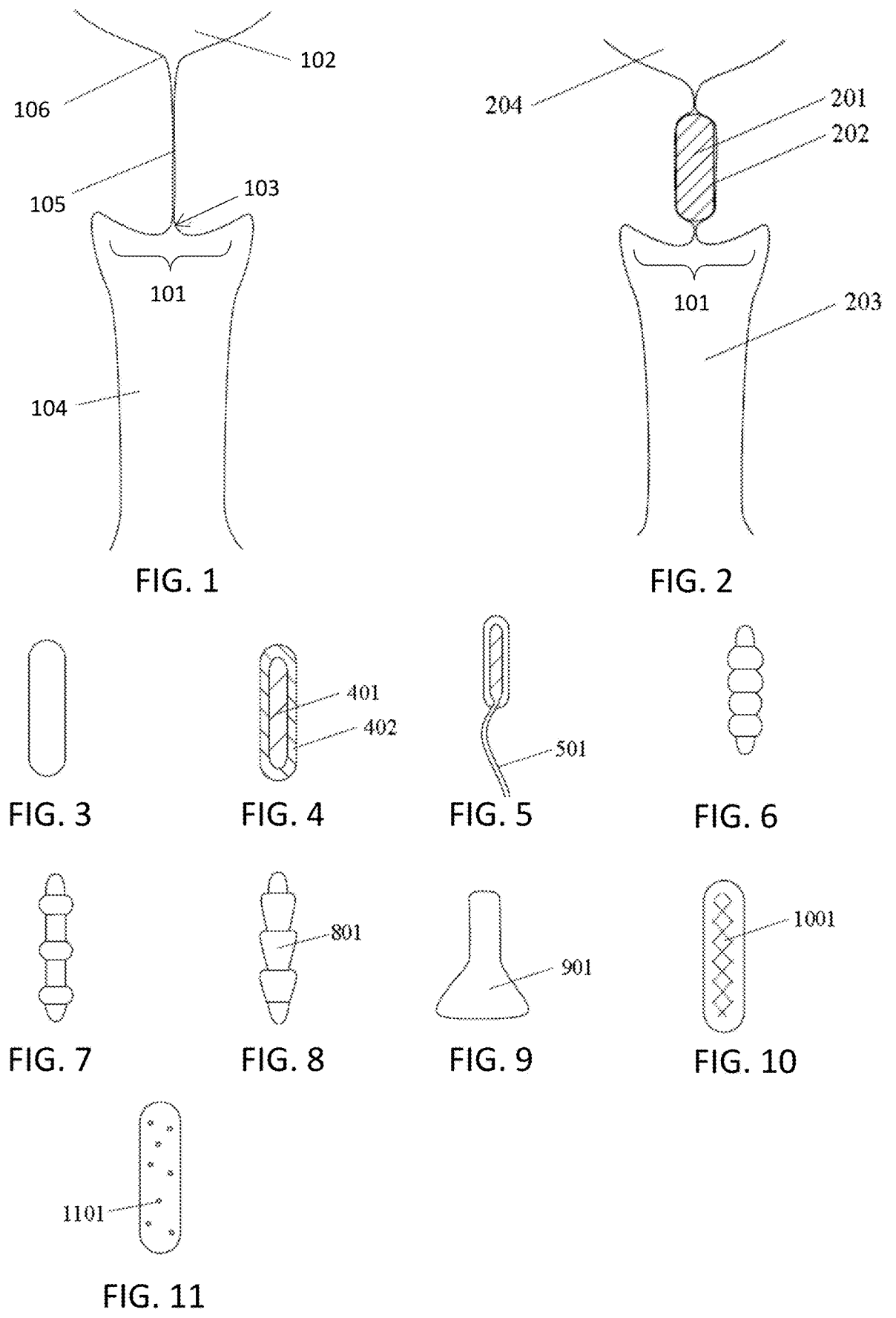

In general, an example of the anatomical features and regions associated with the human female reproductive system referred to herein are illustrated in FIG. 1, including uterine cavity 102, cervical canal 105 external os 103, internal os 106, and vagina 104. The ectocervix (as described herein, referring to the vaginal face of the cervix) is shown in 101; the opening into the cervical canal is shown in a middle region of the ectocervix. Although in general the disclosure described herein includes forming a microbial barrier on the ectocervix 101 while preventing disturbing the vaginal canal and thus a mucus plug (not shown), in some variations an additional or alternative occlusive member may be inserted in the cervical canal. FIG. 2 is an example of the anatomy of the vagina, cervix and uterus of a pregnant woman, showing an occlusive element 201 positioned within cervical canal 202. In some embodiments, occlusive element 201 is wholly contained within cervical canal 202. In some embodiments, part of occlusive element 201 extends into vagina 203. In some embodiments, part of occlusive element 201 extends into uterine cavity 204.

FIGS. 3 through 11 show a variety of embodiments of such occlusive elements. For example, FIG. 3 shows an embodiment of occlusive element with generally rounded ends and a generally cylindrical long region that is circular in cross-section. In some embodiments, occlusive elements may have one or more of the following cross-sectional shapes: circular, oval-shaped, a cross-section that approximates a cross-sectional shape of a cervical canal, vaginal canal, or uterine cavity. In some embodiments, occlusive elements may have a variable cross-sectional shape along their length.

FIG. 4 shows an occlusive element, featuring a stiffening structure 401 and a softer structure 402. Stiffening structure 401 may help maintain a desired shape of the occlusive element, while softer structure 402 may improve comfort and/or approximate the internal shape of the cervical canal. In some embodiments, stiffening structure 401 is made of one or more of the following: biocompatible polymers, hydrogels, Nitinol, stainless steel, plastics, fabric, foam. In some embodiments, softer structure 402 is made of one or more of the following: biocompatible polymers, hydrogels, Nitinol, stainless steel, plastics, fabric, foam. In some embodiments, stiffening structure 401 is made of substantially the same material as softer structure 402, but has a higher density and/or stiffness than softer structure 402. For example, stiffening structure 401 may be made of a foam material with a first porosity, and softer structure 402 may be made of the same foam material with a second porosity, wherein the second porosity may be greater than the first porosity.

FIG. 5 shows an occlusive element with removal-enabling feature 501. Removal-enabling feature 501 may be a string or filament that protrudes from the occlusive element, in the general direction of the vaginal opening. Removal-enabling feature 501 may be cut to a shorter length prior, during, or after implantation of the occlusive element. In some embodiments, removal-enabling feature 501 becomes secured to or partially within an occlusive element as an occlusive element hardens. In some cases, a removal-enabling feature is a magnet that is magnetically attracted to a separate magnet on a removal instrument inserted into vaginal canal to remove the occlusive element.

FIGS. 6 and 7 show an occlusive element with a cross-sectional shape varying along the length of the occlusive element. In some cases, the varying comprises alternating increases and decreases in cross-sectional area, diameter, or another key parameter that at least partially defines the cross-section. The varying may occur along the full length of the occlusive element, or along part of the length of the occlusive element.

FIG. 8 shows an occlusive element with at least one geometric feature 801 that prevents migration of the occlusive element in an undesired direction, and/or promotes migration of the occlusive element in a desired location. The geometric feature 801 may interact with the wall of the cervical canal in a manner that results in a normal force between the feature and the wall of the cervical canal that is directed non-perpendicularly to the general axial path of the cervical canal.

FIG. 9 shows an occlusive element with a location-preserving feature 901. In the shown embodiment, the location-preserving feature 901 mechanically interferes with the anatomy at the entrance or exit of the cervical canal, thus preventing unwanted migration of the occlusive element and/or providing feedback about the occlusive element's location to an individual implanting the occlusive element. In some embodiments, the location-preserving feature 901 has one or more of the following kinds of shapes, or has one or more of the following kinds of shapes with regions of missing material: conical, spherical, ovoid, disc-shaped, flange-shaped, arm-shaped. In many embodiments, the location-preserving feature 901 creates a major dimensional characteristic, such as diameter, length, or cross-sectional area, at its site along the length of the occlusive element, that exceeds a corresponding dimensional characteristic at a separate site along the length of the occlusive element intended to be contained within the cervical canal.

FIG. 10 shows an occlusive element with a surface 1001 intended to promote a desired effective coefficient of friction between the occlusive element and the wall of the cervical canal. In some embodiments, the desired texture of surface 1001 is smooth, and may function, for example, to allow easier insertion into the cervical canal. In some cases, the occlusive element may be coated with (or made with) a material, such as PTFE, to make surface 1001 smooth, or to achieve a lower coefficient of friction between surface 1001 and the wall of the cervical canal. In some cases, it may be desired that surface 1001 interact with the cervical wall in a manner that prevents or minimizes migration; in these cases, a not especially smooth finish of surface 1001, and/or a higher coefficient of friction between surface 1001 and the wall of the cervical canal, may be desired. The not especially smooth finish of surface 1001 may be achieved by featuring one or more of the following on at least part of the surface of the occlusive element: grooves, indentations, ribs, augmentations, crisscrossing grooves. The higher coefficient of friction between surface 1001 and the wall of the cervical canal may be achieved by coating (or making) the occlusive element with a higher-friction material, such as medical-grade rubber.

FIG. 11 shows an occlusive element configured to release a material through channels such as channel 1101. In some cases, the material is an antibiotic intended to prevent or reduce the prevalence of one or more kinds of bacteria. In some cases, the material is a probiotic intended to promote or maintain the prevalence of one or more kinds of bacteria. In some cases, the material comprises a microbiota transfer from a donor. In some cases, the material is stored in a reservoir at least partly contained within the occlusive element. In some cases, the material is at least partly contained within a coating on the surface of the occlusive element. In some cases, channels such as channel 1101 are unnecessary and not present in the occlusive element.

In general, the cervical canal barrier implants illustrated in FIGS. 3-11 may be used by themselves to form a microbial barrier, or they may be used with an ectocervical microbial barrier applied to the ectocervix, as described in detail herein. Alternatively, in some variations the ectocervical barriers (microbial barrier or film applied to an ectocervix) may be applied without inserting anything (and in particular a barrier implant) into the cervical canal; indeed, the cervical canal may be avoided entirely in order to prevent disturbing any mucus plug that may be present and/or the uterus. When used with an ectocervical barrier, the implant may be inserted into the cervical canal first, prior to application of the microbial barrier to the ectocervix of a cervix.

In some variations a barrier implant is inserted as a liquid, semi-solid (e.g., gel, etc.) and allowed to harden upon insertion. FIG. 12 illustrates an occlusive element 1201 provided via a delivery member 1202 to a site at least partially within a cervical canal. For example, the material of at least part of the occlusive element is in a liquid, gel, or softened state prior to delivery; in some cases, the material is contained within an injecting tool 1203 (such as a syringe) coupled to the delivery tube. In some cases, the delivery member is a tube. In some cases, the delivery tube has an augmentation 1204, which in some cases prevents over-insertion of the delivery member into the cervical canal. In some cases, the augmentation 1204 isolates a first region where the occlusive element is desired to be present from a second region where the occlusive element is not desired to be present. In a variation of the invention shown in FIG. 12, the augmentation 1204 may be positioned at a site on delivery member 1202 that is distal to the site on delivery member 1202 from which the occlusive element 1201 is released; in this variation, the augmentation 1204 prevents the occlusive element 1201 from reaching a site distal to its intended site. In some cases, augmentations are placed both distal and proximal to a desired site of an occlusive element, and in some cases, prevent an occlusive element from assuming a position proximal or distal to a surface of the augmentation. In some cases, augmentations help form at least part of the shape of the occlusive element, in some cases as the occlusive element hardens. In some cases, augmentation 1204 is a soft material that compresses against surrounding tissues. In some cases, augmentation 1204 is an inflatable member, expanded using a gas or liquid injected via a lumen passing through delivery member 1202. In some cases, augmentation 1204 is not present on delivery member 1202. In some cases, the occlusive element is advanced through the delivery member using a pusher (not shown in FIG. 12), which may render injecting tool 1203 unnecessary. In some cases, the system shown in FIG. 12 or variations thereof are used in conjunction with one or more of the following: a hysteroscope, a speculum, a tissue-grasping tool.

The material that may comprise at least part of occlusive element 1201 may be prepared shortly before the delivery into a cervical canal, in some cases by mixing two or more ingredients that were previously unmixed. In some cases, a removal-enabling feature is positioned in the cervical canal, then material forming an occlusive element is injected into the cervical canal, at least partially encapsulating the removal-enabling feature. The materials forming any of the occlusive implants described herein may also be the same as the materials forming the microbial barrier to an ectocervix of a cervix, described herein (and vice-versa).

A delivery sheath may be used to deliver an occlusive implant and/or film. For example, FIGS. 13 and 14 show section views of a device for positioning a delivery sheath within an anatomical region, in some cases within the female reproductive system. In some cases, the device prevents at least part of a delivery sheath 1301 from contacting a first proximal location along a vaginal wall or cervical canal before contacting a second distal location along a vaginal wall or cervical canal, thereby reducing the likelihood that microorganisms are moved from the first proximal location to the second distal location by placement of the device. In the embodiment shown, delivery sheath 1301 is coupled at coupling site 1302 to component 1303, which may feature a flange 1304 that aids in handling and/or prevents over-insertion of component 1303 into the vagina or cervical canal. Force-transmitting feature 1305 is advanced from a first position (depicted in FIG. 13) to a second position (depicted in FIG. 14), causing the delivery sheath 1301 to unfurl. In some embodiments, a stopper 1306 engages with component 1303 to prevent over-advancement of force-transmitting feature 1305; in other embodiments, stopper 1306 is not present. Thus in some variations the sheath may be used to protect the anatomy when inserting an occlusive implant and/or microbial barrier to an ectocervix of a cervix.

In some embodiments, the relative lengths of force-transmitting feature 1305 and delivery sheath 1301 are chosen to prevent force-transmitting feature 1305 from extending past delivery sheath 1301.

Marks on force-transmitting feature may provide indication of the depth of penetration of delivery sheath 1301 and/or force-transmitting feature 1305.

Coupling site 1302 may vary from the site depicted in FIG. 13 and FIG. 14; for example, coupling may occur at one or more of the following: the outside wall of component 1303, the inside wall of component 1303, the distal end of component 1303. In some embodiments, delivery sheath 1301 is mechanically biased, at least partly, to an unfurled position. In some embodiments, delivery sheath 1301 is mechanically biased, at least partly, to a furled position. In some cases, the non-distally-extended configuration of delivery sheath 1301 is one or more of the following: a rolled configuration, a folded configuration, a bunched configuration, a proximally-extended straightened configuration.

FIG. 15 shows another view of a device for positioning a delivery sheath, similar to that shown in FIG. 13.

Figure 16:
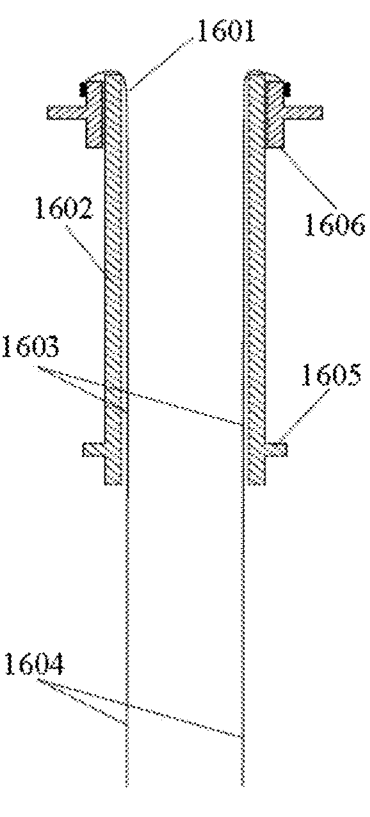
FIGS. 16 and 17 illustrate another variation of a delivery sheath tool in a proximally retracted (FIG. 16) and proximally extended (FIG. 17) configuration, which his reversible, and may be used to deploy/remove the sheath.
Figure 17:
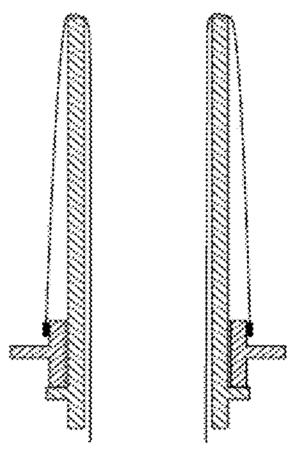

FIG. 16 shows a section view of a delivery sheath 1601 in a proximally-extended straightened configuration. Delivery sheath 1601 may be moved to a distally-extended configuration (shown in section view in FIG. 17) by advancing force-transmitting member 1602. Delivery sheath 1601 may be restored to the proximally-extended straightened configuration of FIG. 16 by providing tension on delivery sheath 1601, for example at a first proximal site 1603 or at a second proximal site 1604. Maintaining a compressive force on force-transmitting member 1602, and a tensile force on delivery sheath 1601 at a proximal site such as first proximal site 1603 or second proximal site 1604, may in turn maintain tautness in delivery sheath 1601. In some embodiments, a tension feature may be coupled to a proximal site (such as proximal site 1603 or proximal site 1604). In some embodiments, the tension feature translates at least partly within, around, or alongside force-transmitting feature 1602. In some embodiments, force transmitting feature 1602 and the tension feature may be one or more of the following: concentric tubes; structures mechanically constrained to translate along a common axis; structures mechanically constrained to not rotate relative to one another; structures slidably disposed to one another.

In some embodiments, stopper 1605 engages with component 1606 to prevent over-advancement of delivery sheath 1601. In some embodiments, stopper 1605 is not present.

Figure 18:
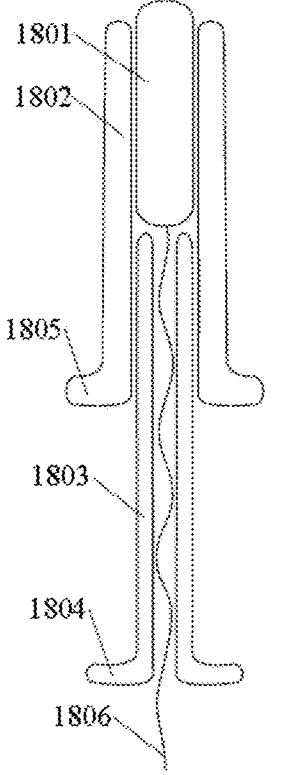
FIGS. 18 and 19 show sectional views of one example of a deployment tool and barrier implant deployable from the tool, in an un-deployed (FIG. 18) and deployed (FIG. 19) state.
Figure 19:
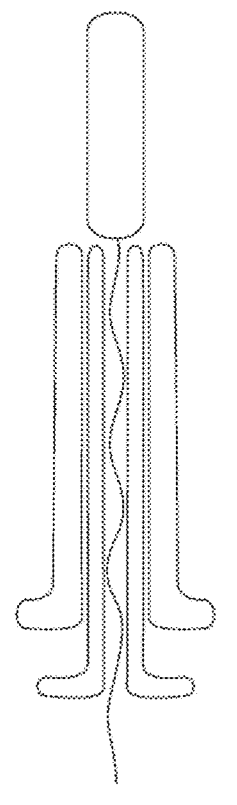

FIGS. 18 and 19 show sectional views of an advancement tool for occlusive element 1801, comprising casing 1802, and pusher 1803. In some cases, the advancement tool is inserted into the vagina and/or cervix. In some cases, occlusive element 1801 is advanced and/or released, by moving pusher 1803 from a first position (represented in FIG. 18) at least partially within casing 1802 to a second position (represented in FIG. 19) outside of casing 1802. In some cases, pusher 1803 is maintained in a substantially constant position relative to a patient (for example, a substantially constant position within a vagina or cervical canal), and the casing 1802 is retracted, releasing the occlusive element 1801. In some cases, pusher flange 1804 mechanically interferes with casing 1802, or a feature connected to casing 1802, such that pusher 1803 cannot be over-advanced (or casing 1802 over-retracted). In some cases, pusher flange 1804 is absent, and over-advancement of pusher 1803 is prevented by mechanical interference between casing 1802 and pusher 1803 elsewhere. In some cases, a removal feature 1806 (which may be a string) extends proximally from the occlusive element 1801, through the pusher 1803 and/or the casing 1802. In some cases, casing flange 1805 prevents over-insertion of the advancement tool into the vaginal or cervix, and/or makes handling of the advancement tool easier. In some cases, a distal feature on casing 1802 partly or fully isolates occlusive element 1801 from contact with vaginal or cervical tissues until pusher 1803 is advanced relative to casing 1802.

FIG. 20 shows delivery of an occlusive barrier 2001 to an external surface of a cervix 2005 with a delivery system 2006 comprising a syringe 2003 coupled to a delivery lumen (not shown) that extends through an elongate body 2007. In some cases, an operator may insert a speculum or forceps into the vagina prior to inserting the delivery system 2006. In some cases the operator may reposition the cervix 2005 before delivering the occlusive element 2001. The operator may position locating features 2004 of the delivery system 2006 in contact with a convex surface of the external surface of the cervix 2005 to center the delivery system 2006 for delivery of the occlusive element 2001. The locating features may be composed of a flexible material such as silicone and may be retracted and/or folded during insertion into the vagina. The occlusive barrier 2001 may be a film, coating, layer, membrane, or the like, which is applied as a microbial barrier to an ectocervix of a cervix. Alternatively or additionally the barrier may be a mesh, membrane, frame, etc. that is applied to the ectocervix. In some variation a coating may be applied with a frame; the frame may provide additional support and/or may limit or guide the application of the coating, including protecting other anatomical regions such walls of the vagina and/or the opening into the cervical canal. As described and illustrated herein, this microbial barrier to an ectocervix of a cervix may be applied as a liquid or gel. For example in FIG. 20, the barrier may be a gel delivered from a syringe 2003, wherein after exiting the delivery lumen, the occlusive element 2001 may increase in viscosity due to a chemical reaction. In some cases the occlusive barrier 2001 may be delivered as a spray from a spray tip (not shown) of the delivery system 2006. The apparatus may include a cup-shaped applicator head (e.g., which may be a concave shaping feature) 2002 to confine the occlusive element 2001 for a period of time as the occlusive element 2001 increases in viscosity. After the operator removes the delivery system 2006, a portion of the occlusive element 2001 may comprise a shape formed with the concave shaping feature 2002. The concave shaping feature 2002 and/or other components of the delivery system 2006 may contain at least one surface (e.g., an inner, tissue-facing surface) which is non-adhesive and may be coated or treated to reduce adhesion to the occlusive coating 2001 formed on the ectocervix. For example, the concave shaping feature 2002 may have a Teflon-coated surface to minimize adhesion to the occlusive element 2001, which may comprise a sealant. As will be described in more detail herein, any of these variations may also include a baffle, or other protective region to prevent direct application of the coating material into the cervical canal.

Any of these apparatuses may also include one or more locating features, which may be extension of the cup-shaped applicator head (e.g., arms, wings, etc.) or may be separate from the cup-shaped applicator, and ma generally help position the applicator head relative to the outer, vaginal-face of the cervix (the ectocervix). For example, a distal portion of the delivery apparatus 2006 in FIG. 20 may include locating features 2004 and the concave shaping feature 2002. Any portion of the applicator, and particularly the distal cup-shaped region, may be configured so that cervix can be visualized and/or imaged when the apparatus is applied to the cervix. For example, a portion (e.g., the cup-shaped housing) may be transparent, to enable visualization of the cervix during application of the occlusive element. In some embodiments, a delivery system for delivery of an occlusive element and/or a coating material may contain at least one component that is translucent or transparent. Alternatively or additionally, the apparatus may include a camera (CCD, etc.) or light path (e.g., fiber optic) for imaging.

In general, the occlusive material is positioned to occupy at least part of a path along which microorganisms might migrate or proliferate to or toward an anatomical region (such as the cervix, cervical canal, and/or uterus) at which their presence is unwanted, for example in order to prevent preterm birth associated with infection and/or inflammation. The device or material may therefore be positioned in the female reproductive system.

Although it may be beneficial to position the barrier only in the external vaginal-facing ectocervix, in some embodiments, an occlusive device/barrier (or material forming the barrier) is positioned partly or fully within a vagina, cervical canal, and/or uterus, in order to isolate a first region where a first type, proportion, quantity, distribution, or proliferation of a microorganism is suspected to be or to become present, from a second region where the first type, proportion, quantity, distribution, or proliferation of the microorganism is unwanted. The device (including applicator device) may comprise one or more of the following: (a) a contacting element, which imparts frictional and/or normal force to the vaginal wall and/or ectocervix of the cervix, or which otherwise maintains a position within the vagina; (b) a material, at least some of which occupies at least part of a path along which microorganisms migrate or proliferate to or toward an anatomical region (such as the cervix, cervical canal, and/or uterus) at which their presence is unwanted; (c) a containing region, which holds at least some of the material; (d) material insertion sites, where the material is delivered to the containing region before, during, and/or after the device is positioned; (e) egress sites (e.g., lumen through the applicator device), where liquid, gas, or the coating material can pass from the device (for example, from a containing region); (f) a delivery driver (e.g., syringe, pressure source, etc.), which may be used to deliver coating material into the containing region and/or to position and/or release the device; (g) a delivery tool, used to deliver the coating material and/or device; and (h) a handle or other handling feature, used to hold and/or position the device.

Some of the elements listed above may be integrated and/or combined, and may be fully or partially not distinct from one another. Non-limiting examples include the following: material insertion sites may also serve as egress sites; a contacting element may also serve as part of a containing element; and a handling feature may also serve as part of a containing element.

In some embodiments, in addition to isolating the first region from the second region, the device provides at least some of the known and/or hypothesized effects and/or benefits of a cervical pessary or cervical cerclage, some of which may prevent preterm birth. For example, the barrier device (e.g., film and/or implant) may prevent and/or postpone premature or unwanted dilation and/or effacement of the cervix, and/or funneling at the internal orifice of the uterus; the barrier device may promote or maintain a more closed cervix; the barrier device may prevent the need for cervical cerclage, and prevent associated clinical complications or stitch removal procedures; the barrier device may effectively lengthen the cervix, and/or bend the cervix backward; the barrier device may alter the uterocervical angle, which may help protect membranes from contact with other tissues that could compromise the membranes' structural integrity; and/or the barrier device may prevent pelvic organ prolapse.

A barrier device may, across a number of embodiments, feature a number of shapes. Some of these shapes may be typical of vaginal or cervical pessaries. Such barrier devices may, in particular, be used in addition to or to supplement a barrier coating as described herein. For example, a barrier device could be, for example: ring-shaped, disc-shaped, donut-shaped, circular, stairstep-shaped, oval-shaped, conical, helmet-shaped, cup-shaped, cap-shaped, and/or partially shaped as such. The barrier device could, for example, include an augmentation along part of its profile that provides a different force profile in at least one region of tissue contact than in at least one other region of tissue contact. The device could, for example, have a region, such as a hole, which fits around the ectocervix of the cervix. The device could, for example, be sigmoidal in shape, when viewed from at least one angle. In some embodiments, an element of the device could trace a path that is generally circular or oval-shaped when viewed from a first direction, and is generally planar when viewed from a direction orthogonal to the first direction.

In some embodiments, a containing region is bounded at least in part by a barrier device, and at least in part by cervicovaginal tissues. For example, the material may contact the containing element as well as the vaginal wall and the ectocervix of the cervix.

The barrier-forming material (coating material) may be delivered to a site in the vagina (e.g., to apply the coating to the ectocervix), and the applicator device or tool may subsequently positioned to help maintain the location of the barrier coating material. In some embodiments, the applicator device is delivered to a site in the vagina, and the material is subsequently delivered (for example, at material insertion sites). In some embodiments, prior to device placement in the vagina, the coating material is loaded or otherwise placed in the containing region of the device, and the device is subsequently delivered to a site in the vagina. In some cases, the applicator device is refilled or reloaded with coating material one or more times after the device is positioned. In any of the variations described herein, multiple coatings and/or implants may be delivered (in some cases, days or weeks after initial device delivery). In some cases, a new device replaces a previously placed device, or they may be added to the already-applied/inserted devices/coatings.

In some embodiments, in which the coating or implant-forming material is placed in a containing region of the applicator device prior to delivery, positioning of the device in the vagina results in the displacement of at least some of the material by tissues (for example, the ectocervix of the cervix). In some cases, configuring the material in the containing region and/or configuring the containing element such that displacement of at least some of the material occurs during positioning helps ensure that material is adjacent to tissue, which may more effectively proliferation or migration of microorganisms from a first region to a second region at which their presence is unwanted.

The apparatuses described herein may be delivered and/or positioned with the aid of a delivery tool, such as forceps. In some cases, a medical professional may deliver the device; in some cases, the wearer of the device delivers the device. A speculum (for example, a bivalve vaginal speculum) and/or other gynecological tools may be used to facilitate the placement of the apparatuses, implants, and/or coatings at a desired position.

The insertion tools/devices, implants and/or coatings may feature radio-opaque features or components that aid in visualization.

As mentioned, materials may be positioned partly or fully within a vagina, cervical canal, and/or uterus, in order to isolate a first region where a first type, proportion, quantity, distribution, or proliferation of a microorganism is suspected to be or to become present, from a second region where the first type, proportion, quantity, distribution, or proliferation of the microorganism is unwanted. In particular, a coating may be applied only to the outer face of the cervix in the vagina (e.g., the ectocervix). In some embodiments, the material (e.g., implant material and/or coating material) increases the distance that microorganisms must migrate, or over which they must proliferate, in order to migrate or proliferate from the first region to the second region. In some embodiments, the material includes anti-microbial agents, or possesses anti-microbial properties, that weaken or kill at least some microorganisms. For example, the material may include silver ions and/or chlorhexidine. In some embodiments, the material partly, substantially, and/or fully fills at least a partial volume of the vagina. In some embodiments, the partial volume is located at the far end of the vagina from the vaginal opening; in some embodiments, the partial volume is located closer to the vaginal opening.

In some embodiments, the material is prepared by mixing at least two substances prior to delivery of the material into the vagina and/or into the device. In some embodiments, at least two substances (for example, two chemicals) reside in at least two starting chambers (for example, two syringes), and are combined when they are injected into a common chamber, passageway, and/or volume. In some embodiments, the common chamber, passageway and/or volume is configured to promote mixing of the at least two substances. In some embodiments, the at least two starting chambers, and/or the common chamber or passageway, are part of a delivery system. In some cases, material is prepared (for example, at least two substances are mixed to prepare the material) not long before the material is delivered into the vagina.

In some embodiments, the device comprises a structure that is soaked with the material or otherwise contains the material, and the device is placed within the vagina. The structure exerts force on the vaginal wall that helps maintain a desired location of the device, and the material acts to interrupt and/or occupy a potential path of migration or proliferation of microorganisms. In some cases, the structure is sponge-like.

In some embodiments, the device contains data acquisition, data storage, and/or data transmission components, which may measure temperature, pH, wetness, strain, or other parameters, some or all of which may be used to track a patient's health and/or metrics related to pregnancy.

In some embodiments, egress sites prevent material from becoming pressurized beyond a desired level. In some embodiments, egress sites allow material to migrate into a closed region that expands, stretches, enlargers, or otherwise accommodates an increasing volume of material.

In some embodiments, the material may comprise a gel, liquid, mixture, colloid, foam, solution, and/or suspension. In some embodiments, the material may comprise one or more of the following: a biocompatible polymer, keratin, cyanoacrylate, bismuth subnitrate (in some cases, in an oil base), bioresorbable materials, ethylene vinyl copolymer dissolved in dimethyl sulfoxide, poly (vinyl acetate-ethylene) copolymer clear thermoplastic, polyurethane, polyethylene, PTFE, clay, kaolinite, alginate, silk, hydrogel, polyethylene glycol, glycerin, glyceryl polymethacrylate, propylene glycol, guar gum, paraffin, liquid paraffin, petroleum jelly, mineral oil, glycerol, ethylene-glycol stearate, lanolin, and silicone-based gel. In some embodiments, the material may comprise both oil-based and water-based components.

In some cases, the material assumes a shape of a volume bounded at least in part by the interior of the vagina, cervical canal, and/or uterus. In some embodiments, the material may possess a high viscosity, which may facilitate retention of the material in a desired location after delivery. In some embodiments, an attribute of the composition of the material may be selected such that absorption and/or resorption of the material is reduced or augmented. For example, liposolubility, molecular weight, electronic structure, dissociation constant, and/or polarity of at least a portion of the material may be selected such that absorption of the material is limited. In some embodiments, the material has high tissue conformability. In some embodiments, the material adheres to cervicovaginal tissues.

The material may contain a colorant. For example, the material may contain a biocompatible blue colorant to aid in visualization of the material.

FIG. 21 shows a representation of a portion of a female reproductive system, including vagina 2101, vaginal wall 2102, ectocervix 2100, external os of the cervix 2103, cervical canal 2104, and uterine cavity 2105.

FIG. 22 shows an implant 2201 and coating 2206 positioned in vagina 2101 to prevent microorganisms in vagina 2101 from migrating and/or proliferating into cervical canal 2104 and/or uterine cavity 2105, and/or interacting in an unwanted manner with cervical or uterine tissues. In the embodiment shown in FIG. 22, implant device 2201 comprises a contacting element 2202, a containing element/region 2203, a containing region 2204, a handling feature 2205, and a coating material 2206. Contacting element/region 2202 imparts normal force and/or frictional force on a region of vaginal wall 2102, from which results opposing normal force and/or frictional force on contacting element/region 2202 that disfavors migration of device 2201 toward the opening of vagina 2101, and/or favors a stable position of implant device 2201 in the distal region of the vagina 2101 (in some cases, in a position near, adjacent to or surrounding the ectocervix of the cervix). Containing element/region 2203 of the device acts to maintain a position of coating material 2206 adjacent to or surrounding the ectocervix of the cervix. Containing element/region 2203 may be shaped to form containing region 2204, wherein coating material 2206 at least partially resides. Handling feature 2205 may aid in the delivery, adjustment, and/or removal of implant device 2201 and/or coating. Coating material 2206 may interrupt, slow, and/or prevent the migration and/or proliferation of microorganisms from vagina 2101 into cervical canal 2104 and/or uterine cavity 2105, and/or to sites contacting cervical or uterine tissue.

FIG. 23 illustrates another example of an implant device 2201 and coating material, in which contacting region 2202 of the implant imparts normal force and/or frictional force on the ectocervix of the cervix 2103, from which results opposing normal force and/or frictional force on contacting element 2202 that prevents migration of the implant device 2201 toward the opening of the vagina 2101, and/or favors a stable position of the implant 2201 in the distal region of vagina 2101 (in some cases, in a position near, adjacent to or surrounding the ectocervix of the cervix). Containing region 2203 of the implant may be shaped to form a containing region 2204, wherein coating material 2206 at least partially resides.

Figure 24:
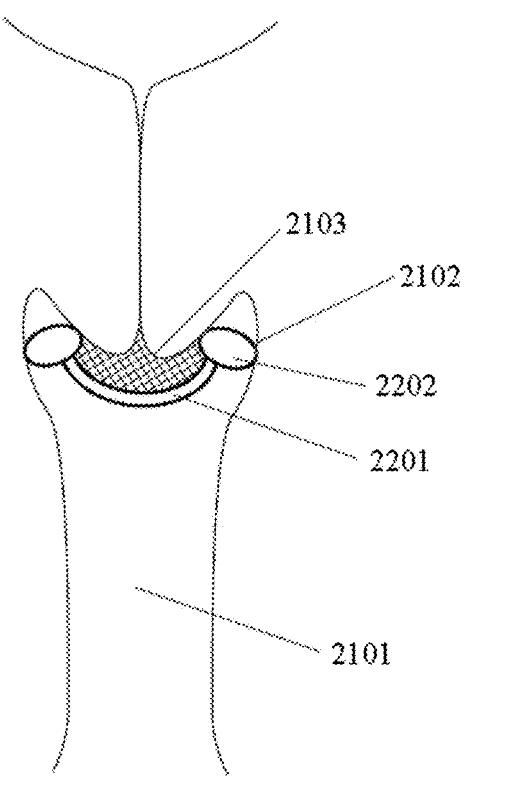
FIG. 24 illustrates another example of a microbial barrier coating applied to an ectocervix with an implant structure that may be removed after forming the coating or left in place.

FIG. 24 illustrates another example of a combined implant and coating material. In FIG. 24, the implant 2201 includes a contacting region 2202 that imparts a normal force and/or frictional force on a region of vaginal wall 2102, from which results opposing normal force and/or frictional force on contacting region 2202 that prevents migration of the implant 2201 toward the opening of vagina 2101, and/or favors a stable position of device 2201 in the distal region of 2101 (in some cases, in a position near, adjacent to or surrounding the ectocervix of the cervix); and may also impart a normal force and/or frictional force on the ectocervix of the cervix 2103, from which results opposing normal force and/or frictional force on contacting element 2202 that disfavors migration of device 2201 toward the opening of vagina 2101, and/or favors a stable position of implant 2201 in the distal region of vagina 2101 (in some cases, in a position near, adjacent to or surrounding the ectocervix of the cervix).

Figure 25:
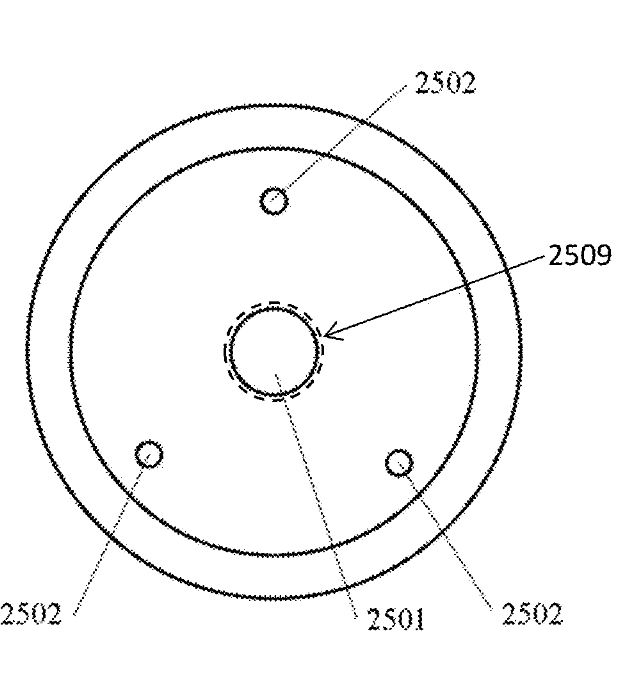
FIG. 25 shows an example of a concave inner region of a structure used to form a microbial barrier. The inner region shown in FIG. 25 may be part of an implant and/or part of an applicator device (e.g., the inner surface of a cup-shaped applicator at the distal end of an apparatus for forming the coating).

FIG. 25 illustrates one example of a containing insert 2203, featuring material insertion sites (apertures 2501) and egress sites 2502. Material insertion sites 2501 are one or more ports, holes, and/or passageways through which coating material 2206 may be delivered to containing region 2204. Egress sites 2502 in this example may be one or more ports, holes, or passageways through which air, gas, bodily liquids, introduced liquids, and/or coating material 2206 can pass. In some embodiments, material insertion site 2501 is sized or configured to engage with a syringe, tube (such as a catheter), or other member, from which material 2206 may be transferred to containing region 2204. The coating material insertion site 2501 may include a baffle, deflector or other structure so that coating material is ejected from the insertion site at an angle relative perpendicular, to avoid injecting material directly (e.g., with any force/pressure) into the cervical canal. For example, the insertion site (aperture 2501) may be recessed behind a deflector/baffle (2509, dashed lines) in such examples. In some embodiments, egress sites 2502 are located a distance (as measured absolutely, or relative to the path of material 2206 inserted through material insertion sites 2501) from insertion sites 2501 that delays egress of material 2206 until containing region 2204 is desirably (for example, completely or near completely) filled, which may promote more substantial filling of containing region 2204. For example, egress sites 2502 may be located at or near the periphery of containing element 2203, while material insertion site 2501 may be located at or near the center of containing element 2203. In some embodiments, egress sites 2502 lead to closed volumes bounded by expandable material and/or collapsed material, which can expand and/or uncollapse to accommodate egressing air, gas, bodily liquids, introduced liquids, and/or material 2206. Egress of air, gas, bodily liquids, introduced liquids, and/or material 2206 through egress sites 2502 may fulfill one or more purposes. For example, egress of material 2206 may provide an indication that a desired amount of material 2206 has been delivered to containing region 2204 (for example, an amount sufficient to fill a desired proportion of containing region 2204, such as near all or all of containing region 2204), and/or said indication may provide feedback regarding how much additional material 2206 (for example, no additional material 2206) needs to be delivered. In other example purposes, egress of air, gas, bodily liquids, introduced liquids, and/or material 2206 may act to (a) relieve pressurization of air, gas, bodily liquids, introduced liquids, and/or material 2206 in containing region 2204, and/or (b) allow displacement of air, gas, bodily liquids, introduced liquids, and/or material 2206 in containing region 2204, as (c) material 2206 is inserted into containing region 2204 (for example, through material insertion site 2501), and/or (d) tissues of vagina 2101, cervix, or uterus (such as the ectocervix of the cervix) occupy part or all of containing region 2204 during positioning of device 2201 in a vagina. In some cases, relieving pressurization of air, gas, bodily liquids, introduced liquids, and/or material 2206 acts to prevent migration of material 2206 to unwanted positions within cervical canal 2104 and/or uterus, and/or prevents disruption of cervical mucus and/or amniotic tissues.

In some variations the implant of FIGS. 24 and 25 is not implanted, but is integrated into an applicator apparatus (e.g., forming part or all of a cup-shaped applicator head at the distal end of the apparatus).

Figure 26:
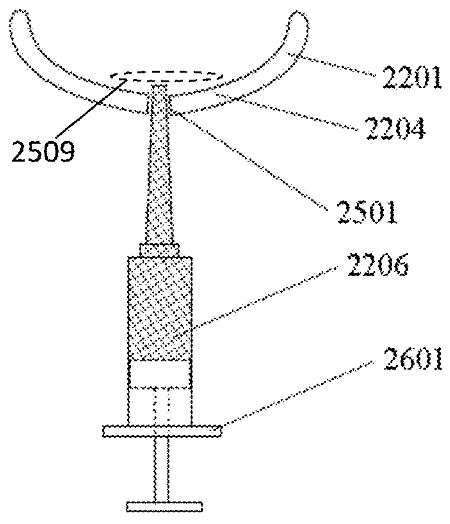
FIG. 26 is an example of an apparatus for delivering an implant and/or coating material on to an ectocervix.
Figure 26:

FIG. 26 shows one example of a delivery apparatus for delivering a coating material, including a syringe 2601, which may be used to deliver an implant 2201 and/or coating material such as those shown in FIGS. 23-25 to a position in a vagina over the ectocervix. In the embodiment shown in FIG. 26, delivery syringe 2601 contains material 2206 and is coupled to material insertion site 2501 of device 2201. Upon delivery of device 2201 to a desired position (for example, a location in the distal vagina, with the ectocervix of the cervix occupying at least part of containing region 2204), coating material 2206 may be injected through material insertion site 2501 into containing region 2204.

Figure 27:
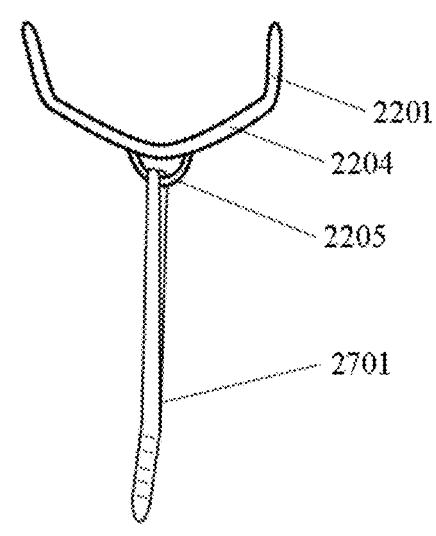
FIG. 27 is an example of a delivery tool as described herein.

FIG. 27 shows a delivery tool 2701, which may be manually operated to grip device 2201. In the embodiment shown in FIG. 27, delivery tool 2701 grips handling feature 2205. Upon delivery of device 2201 to a desired position (for example, a location in the distal vagina, with the ectocervix of the cervix occupying at least part of containing region 2204), delivery tool 2701 may be operated to release handling feature 2205. In some cases, material 2206 is positioned in containing region 2204 of device 2201 prior to delivery of device 2201 to a desired position in a vagina; in some cases, material 2206 is delivered to containing region 2204 of device 2201 after delivery of device 2201 to a desired position in a vagina. Some embodiments of delivery tool 2701 resemble and/or operate in a manner similar to forceps, and some embodiments of delivery tool 2701 are used to delivery an embodiment of device 2201 that lacks a distinct handling feature 2205.

FIG. 28 shows an embodiment of an implant device 2201. In the embodiment of device 2201 shown in cross-section in FIG. 28, the implant device 2201 is ring-shaped.

FIG. 29 shows an occlusive element 2904 covering an ectocervix 2906. In general, the occlusive implant and/or coating may form a mechanical barrier between the vagina 2905 and uterine cavity 2901. In some embodiments, the occlusive implant and/or coating 2904 is attached to the ectocervix 2906 with an adhesive bond. In some embodiments and methods, an operator may elect to leave the cervical mucus plug 2903 in the cervical canal 2902 prior to deploying the occlusive element 2904. As mentioned, alternatively, in some embodiments and methods, an operator may elect to modify, move, and/or remove at least a portion of the cervical mucus plug 2903 prior to deploying the occlusive coating and/or implant 2904. It may be advantageous for the occlusive element 2904 to not impede visual assessment of the ectocervix 2906 and/or other features of the female reproductive tract. In some embodiments, at least a portion of an occlusive element and/or a coating material may be formulated to be translucent or transparent.

In some variations the central region of the ectocervix forming the opening into the cervical canal may not be coated or covered by an implant. For example, FIG. 30 shows an occlusive coating 3004 covering a region of the ectocervix 3001. The occlusive coating 3004 leaves at least one path from the vagina 3005 into the cervical canal 3002 unobstructed. The at least one path left unobstructed may allow the migration of nutrients, molecules, bodily fluids, or materials, enable examination of or access to the cervical canal 3002 or cervical mucus plug 3003 and/or may ease delivery of an infant.

In any of the variations described herein, the doctor or medical professional may assess the patient's health and/or medical history to determine if they are a good candidate for the methods and apparatuses described. In particular, it may be particularly useful to treat women who do not have a preexisting vaginal and/or cervical infection (e.g., cervicovaginal infection). FIG. 31 shows a decision flow diagram that may be used to assess whether to treat a patient with one or more embodiments described herein. These apparatuses and methods may be used in a pregnant woman. For example, in step 3101 the patient may be selected as a pregnant woman. Next, the patient's chorioamniotic membranes and/or cervicovaginal microbiota may be assessed in step 3101. For example, the patient's chorioamniotic membranes may be assessed using a non-invasive maker for rupture of chorioamniotic membranes, such as alpha-fetoprotein. The patient's cervicovaginal microbiota may be assessed to determine whether the patient has a reproductive tract infection. If the patient's chorioamniotic membranes are intact and/or assessment of the patient's cervicovaginal microbiota does not indicate a reproductive tract infection, the patient may be labeled as a candidate in step 3104. If the patient's chorioamniotic membranes are not intact and/or assessment of the patient's cervicovaginal microbiota indicates a reproductive tract infection, the patient may be labeled as not a candidate in step 3103. Thereafter, a coating material may be applied as indicated herein (and/or an implant may be applied).

Figures 32, 33, 34:
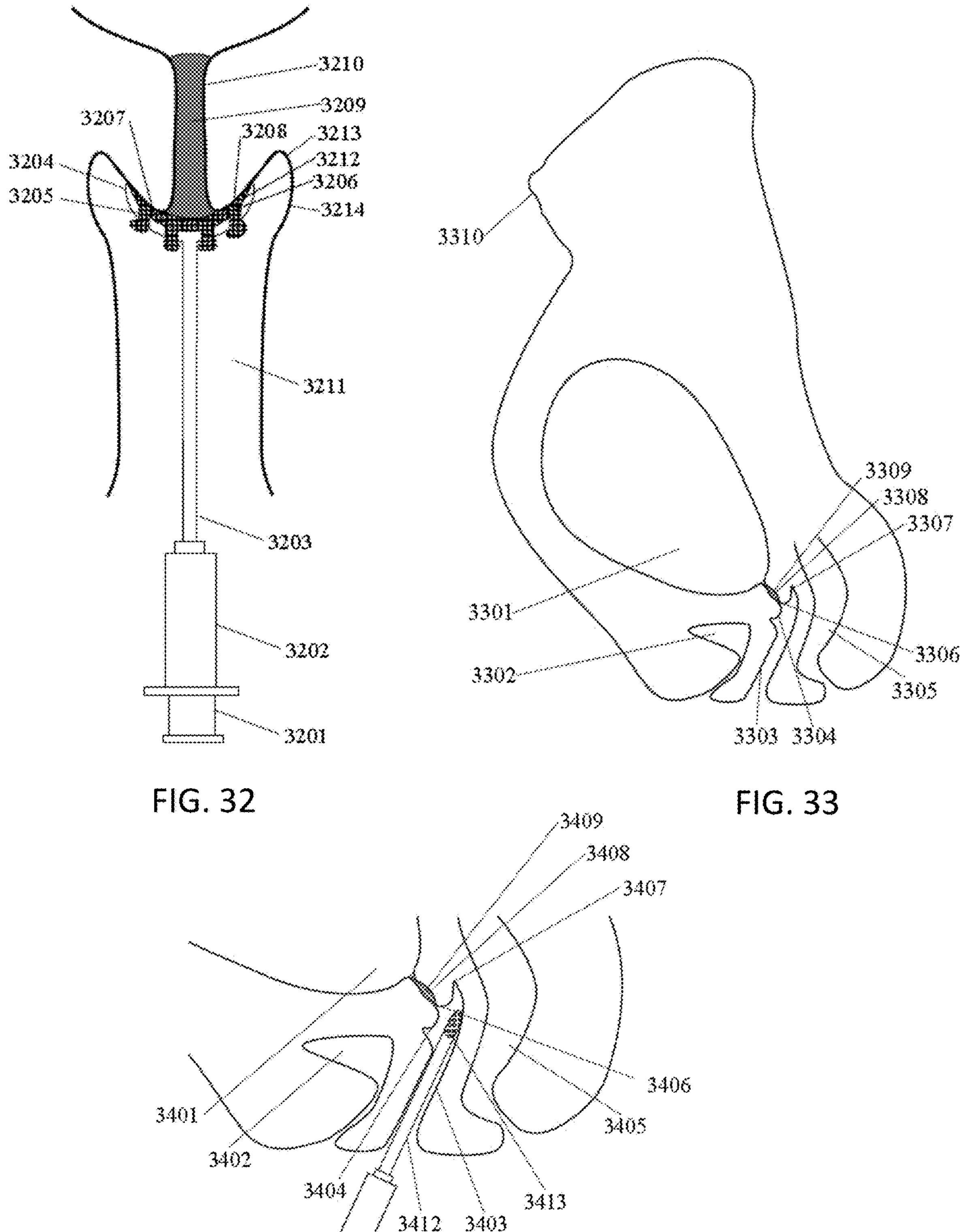
FIG. 32 illustrates one method of delivering an occlusive barrier (e.g., coating) to an ectocervix without disturbing a mucus plug, as described herein.
FIG. 33 is a schematic view through a torso of a woman, indicting the vagina, cervix and uterus in a side view.
FIG. 34 illustrates one method of applying a barrier to the ectocervix of a pregnant woman as described herein.

FIG. 32 depicts delivery of an occlusive element 3207 (e.g., microbial barrier coating and/or implant). An operator inserts in a vagina 3211 of a patient a delivery apparatus 3201 comprising a chamber for coating material (e.g., syringe 3202), an elongate body 3203 featuring a delivery lumen (not shown) and a cup-shaped applicator head (configured as a locating feature 3204). The locating feature 3204 may be utilized to center the distal end of the delivery system with regard to the ectocervix 3208, cervical canal 3210, and/or cervical mucus plug 3209. In some cases, the occlusive element 3207 comprises a sealant. An operator may compress the syringe 3202 to deliver the sealant into a partially sealed volume 3206. One or more egress ports 3205 in the distal end of the delivery system 3201 may enable occlusive element 3207, air, gas, bodily liquids, and/or introduced liquids to exit the partially sealed volume 3206. In some cases, egress of occlusive element 3207, for example sealant, through one or more egress ports 3205 may indicate that a desired amount of occlusive element 3207 has been delivered. In other example purposes, egress of air, gas, bodily liquids, introduced liquids, and/or occlusive element 3207 may act to (a) relieve pressurization of air, gas, bodily liquids, introduced liquids, and/or occlusive element 3207 in partially sealed volume 3206, and/or (b) allow displacement of air, gas, bodily liquids, introduced liquids, and/or occlusive element 3207 in the partially sealed volume 3206, as occlusive element 3207 is inserted into the partially sealed volume 3206. A concave shaping feature 3212 of the cup-shaped distal applicator head may define a portion of the partially sealed volume 3206 and may constrain the occlusive coating material 3207 as it cures. In some cases, the concave shaping feature 3212 may prevent the occlusive coating material 3207 from spanning from the ectocervix 3208 across a fornix 3213 to an upper vaginal wall 3214. Spanning of the occlusive element 3207 from the ectocervix 3208 across the fornix 3213 to the upper vaginal wall 3214 may be undesirable as it may reduce the mobility of the ectocervix 3208 and/or may increase the patient's perception of the occlusive element 3207 during everyday activity.

FIG. 33 shows a cross-section representation of a torso of a pregnant woman, depicting a uterus 3301, a bladder 3302, a vagina 3303, an ectocervix 3304, a rectum 3305, an ectocervix of a cervix 3306, a vaginal fornix 3307, a cervical canal 3308, a cervical mucus plug 3309, and a breast 3310. The cervical canal 3308 may generally not be co-linear with the vagina 3303. In some cases, when an operator attempts to visualize the ectocervix 3304, for example using a speculum (not shown), the ectocervix 3304 may be difficult to locate.

Thus, infection-related pregnancy complications (for example, preterm birth) may be prevented by reorienting the ectocervix of the cervix and the vagina relative to one another; positioning an occlusive device and/or coating delivery device at a location near the ectocervix of the cervix; confirming that the opening of the cervical canal is within a field of application determined at least in part by the occlusive element delivery device and/or the position of the occlusive element delivery device; and delivering the occlusive element (and in some variations, protecting the opening of the cervical canal to prevent disturbing a cervical mucus plug).

Reorienting the ectocervix of the cervix and the vagina relative to one another may comprise changing the angle between the cervical canal and the vagina.

In some embodiments, reorienting the ectocervix of the cervix and the vagina relative to one another reduces the angle between the general path of the vagina and the direction in which the ectocervix of the cervix points. In some embodiments, reorienting may be achieved by applying force, directly or indirectly, to one or more regions of the fornices of the vagina. In some embodiments, reorienting is achieved by applying force directly to the ectocervix of the cervix. In some embodiments, reorienting is achieved by applying force to one or more regions of the vaginal wall; force may be applied and/or maintained, for example, using a speculum, forceps, the occlusive element delivery device, and/or pressurized air.

In some embodiments, positioning of the occlusive element delivery device at a location near the ectocervix of the cervix is performed under direct visualization. In some embodiments, positioning occurs using an endoscope. In some embodiments, positioning is aided by a mechanical feature of the occlusive element delivery device that beneficially interacts with or interferes with the anatomy to, for example: prevent over-insertion, and/or position an ejection site for the occlusive element near the ectocervix of the cervix and/or the opening of the cervical canal. In some embodiments, positioning is aided by one or more markers on the occlusive element delivery device.

In some embodiments, confirming that the opening of the cervical canal is within a field of application of an occlusive material may be determined at least in part by examining a region bounded at least in part by the ectocervix of the cervix and by the occlusive element delivery device. In some embodiments, the examination is performed directly; in some embodiments, the examination is performed using an endoscope. In some embodiments, confirming that the opening of the cervical canal is within a field of application determined at least in part by the occlusive element delivery device is achieved by examining a region outside the field of application to confirm that the opening of the cervical canal, and/or the areas of the ectocervix of the cervix near the opening of the cervical canal, are not found in that region. In some embodiments, the confirming step is unnecessary. In some variations, placement of the applicator apparatus on the ectocervix (as may be defined by the cup-shaped applicator and/or any orientation guides/portions of the applicator device) may reliably orient the apparatus relative to the cervical opening; in general the cervical opening is centrally positioned relative to the ectocervix. The positioning may be configured by visual inspection. Orienting the applicator apparatus relative to the cervical opening may help ensure that any baffles and/or deflection (e.g., the aperture openings in a delivery apparatus) will not apply coating material into the cervical canal with any force/pressure and potentially disturb or disrupt the cervical mucus plug, as mentioned above.

These methods and apparatuses may be configured to include reorienting the ectocervix of the cervix and the vagina relative to one another, positioning an occlusive element delivery device at a location near the external os of the cervix, confirming that the opening of the cervical canal is within a field of application determined at least in part by the occlusive element delivery device and/or the position of the occlusive element delivery device, and delivering the occlusive element are described elsewhere in this application.

FIG. 34 shows a cross-sectional representation of a pelvis of a pregnant woman with one variation of a delivery apparatus 3410 comprising a syringe 3411 and a dispensing/applicator tip 3412 positioned for delivery in a vagina 3403. In this example, a distal end of the dispensing tip 3412 is positioned near an ectocervix 3404 and cervical mucus plug 3409 to deliver an occlusive material (e.g., element or coating material, not shown). The distal end of the dispensing tip 3412 contains a circumferential pattern of delivery ports 3413 for delivery of the occlusive element. In some cases, an operator may compress the syringe 3411, ejecting an occlusive element comprising a sealant through the delivery ports 3413. The circumferential pattern of delivery ports 3413 may facilitate covering a broad area with the occlusive element and/or covering difficult to reach geometry with the occlusive element; for example, the circumferential pattern of delivery ports 3413 may facilitate covering the ectocervix 3404 and cervical mucus plug 3409 occlusive element in cases where the cervical canal 3408 is not co-linear with the vagina 3403. In some cases, a delivery system may contain one or more delivery ports on the dispensing tip 3412 that are located radially relative to the dispensing tip 3412; in some cases, these radial delivery ports are not oriented in a circumferential pattern. In some cases, a delivery system may contain at least one delivery port in line with the dispensing tip 3412 (e.g., oriented axially relative to the dispensing tip 3412). In any of the delivery apparatuses described herein, the distal end region (e.g., dispensing tip 3412) may feature at least one bend, pivot point, hinge point, or the like, which may facilitate navigation of the delivery system to a target location and/or delivery of the occlusive element to a target location. FIG. 34 also depicts a uterus 3401, a bladder 3402, a rectum 3405, an external os of the cervix 3406, and a vaginal fornix 3407.

Figure 35:
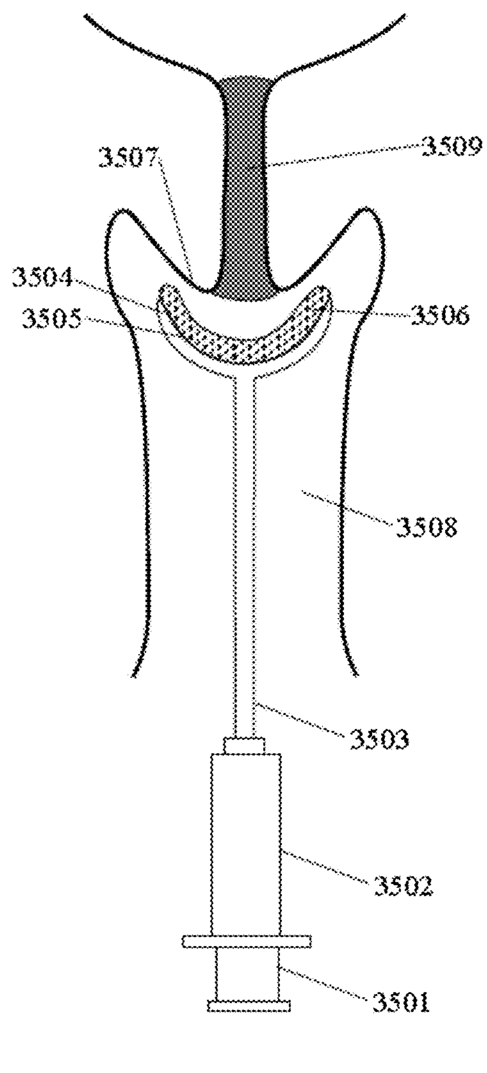
FIG. 35 illustrates the operation of one variation of a microbial barrier applicator device for forming a microbial barrier on an ectocervix in which the applicator includes a baffle (e.g., deflector, buffer, etc.) to limit the pressure and/or force applied to the cervix and particularly to the opening in to the cervical channel to prevent disrupting the cervical mucus plug.

FIG. 35 depicts another example of a delivery apparatus 3501 comprising a syringe 3502, an elongate body 3503 that features a delivery lumen (not shown), a supporting member 3504, and a baffle such as a sponge 3505. The delivery apparatus includes a distal end having a cup-shaped applicator, with an inner chamber forming a concavity into which the baffle is positioned. An elongate body (which may be bent, curbed or curvable) extends between the distal end and the handle region including a chamber (shown here as a syringe) for holding the coating material. A lumen extends between the chamber and the applicator at the distal end. In some cases, the operator may insert the distal end of the delivery system 3501 into a vagina 3508 and position the sponge 3505 in contact with an ectocervix 3507 and/or a cervical mucus plug 3509. The operator may compress the syringe 3502, ejecting occlusive material, for example comprising sealant, into the sponge 3505. The occlusive element may then flow from the sponge onto the ectocervix 3507 and/or cervical mucus plug 3509. The supporting member 3504 may enable an operator to compress the sponge 3505 against a target region, such as the ectocervix 3507 and/or the cervical mucus plug 3509. Delivery of the occlusive element via the sponge may enable one or more of the following: coverage of difficult to access target locations, delivery of a consistent thickness of occlusive element, and repeatable delivery of occlusive element. In some cases, the delivery system may contain a sponge that is pre-impregnated with an occlusive element prior to insertion in the patient. In some cases, the occlusive element undergoes a transition from a lower viscosity to a higher viscosity after application to the patient. For example, an occlusive element comprising a photosensitive sealant may be cured by exposure to light.

Figure 36:
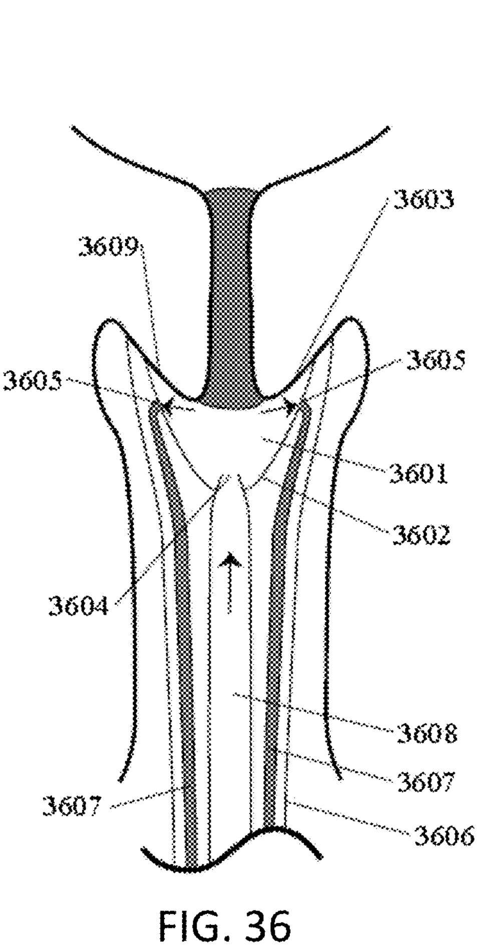
FIG. 36 illustrates another variation of a microbial barrier applicator device for forming a microbial barrier on an ectocervix, including a cup-shaped distal end region forming the barrier and preventing the spread of coating material in lateral regions (e.g., the fornix or walls of the vagina).

FIG. 36 depicts a delivery system 3606 positioned near an ectocervix 3609 of a patient. In some embodiments, a volume 3601 is isolated that is bounded at least in part by the containing arm, channel, or wall(s) 3602 and the tissue intended for coating 3603 (e.g., ectocervix). The coating material (not depicted) enters the volume through one or more entry ports 3604 of the delivery system 3606. The coating material passes through the delivery lumen 3608 to reach the entry ports 3604. The volume 3601 is substantially filled with the coating material. Excess coating material exits the volume through drain ports 3605 into one or more drain lumens 3607. The containing element 3602 may be kept in place for some time to prevent surrounding tissues from disrupting or adhering to the coating before it has adequately cured.

In order to achieve substantial filling prior to draining, the drain ports 3605 may be (a) located relative to the entry ports 3604 such that the volume 3601 must be substantially filled before draining occurs, or (b) of sufficient fluid resistance (a function of coating material viscosity and drain port 3605 geometry and material) that the volume 3601 must be substantially filled prior to draining, for a given rate and pressure of coating material injection.

In some cases, a doctor may decide to conduct a cervical exam on a pregnant woman whose ectocervix had previously been coated with a coating material. It may be advantageous for the coating material to not impede manual assessment of the cervix. For example, it may be advantageous for the coating material to not be so hard it would impede palpation of the underlying cervical tissues. In some embodiments, the coating material is formulated to have a durometer less than Shore A-100; in some embodiments, the coating material is formulated to have a durometer less than Shore A-40. It may be advantageous for the coating material to not be so soft that it would impede palpation of the underlying cervical tissues. In some embodiments, the coating material is formulated to have a durometer higher than Shore 00-5; in some embodiments, the coating material is formulated to have a durometer higher than Shore 00-20. In some embodiments, the coating material is formulated to have a durometer similar to that of the cervix during pregnancy. It may be advantageous for the coating material to not be so thick that it impedes palpation of the cervix. Additionally, it may be advantageous for the coating material to not be so thick that it constrains movement of the cervix during daily activity regular activity; it may be advantageous for the coating material to not be so thick that the presence of the coating material can be perceived by a patient, for example during daily activity regular activity; it may be advantageous for the coating material to be thinner so that there is a smaller volume of material to potentially trigger an inflammatory response. Selection of coating material thickness may depend on coating material properties, including one or more of the following: coating material durometer, coating material fatigue properties, and whether the coating material is pre-formed or not. In some embodiments, the coating material may be less than 2 cm thick; in some embodiments, the coating may be less than 1 cm thick; in some embodiments, the coating material may be less than 5 mm thick. Thickness may be measured perpendicular to tissue, for example ectocervical tissue, to which the coating material is applied. Thickness may refer to a mean thickness, a maximal thickness, or a minimal thickness over subsection or entirety of a coating material. It may advantageous for a coating material to have at least a minimum thickness. For example, a coating material that is composed of a biodegradable hydrogel with a durometer Shore 00-30 may be applied with a sufficient thickness to provide an effective, durable microbial barrier and/or to minimize the likelihood of mechanical failure, such as cohesive failure upon manual examination of the cervix or during movement of the patient. In some embodiments, the coating material may selected to be more than 1 μm thick; in some embodiments, the coating material may selected to be more than 10 μm thick; in some embodiments, the coating material may selected to be more than 1 mm thick. In some embodiments, the coating material may comprise and occlusive element.

Figure 37:
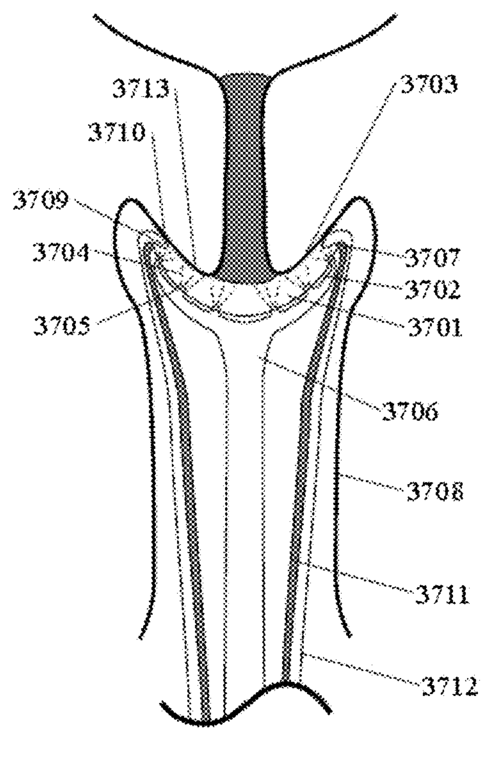
FIG. 37 illustrates another example of a microbial barrier applicator device for forming a microbial barrier on an ectocervix, including a cup-shaped distal end region configured to apply coating material from a plurality of apertures configured to spray (e.g., having spray nozzles) the coating material onto the ectocervix.

FIG. 37 depicts a delivery system 3712 positioned near an ectocervix 3713 of a patient. In some embodiments, a volume 3701 is isolated that is bounded at least in part by a containing element 3702 of the delivery system 3712 and the tissue intended for coating 3703. The tissue 3703 is sprayed with the coating material 3704 through one or more spray ports 3705 in the containing element 3702, which connect via a delivery lumen 3706 to a pressurized reservoir (not depicted) of the coating material 3704 or to components (not depicted) that combine between pressurized reservoirs of the components and the spray ports 3705 to form the coating material 3704. The containing element 3702 may contain vents 3707 that (a) allow air to evacuate from within the containing element 3703, either to the vagina 3708 or into a channel 3711 in the delivery system that runs to outside the vagina 3708, or (b) collect or evacuate excess coating material 3704. The containing element 3702 may also have shields 3709 that prevent coating material 3704 from reaching contact sites 3710 where the containing element 3702 contacts the tissue, reaching areas where the containing element 3702 is within a distance of the tissue that could be easily bridged by cured coating material 3704, or obstructing spray ports 3705. The spray ports 3705 may be configured to achieve a desired distribution of the coating material 3704 on the tissue. The spray ports 3705 may be configured to avoid obstructing a desired view of the tissue. Multiple layers of the coating material 3704 may be applied, in some cases (a) after allowing an earlier layer to at least partially cure, or (b) comprised of different materials that serve different purposes (e.g., adherence to tissue, barrier to microbial passage) to different degrees. Minimizing contact between the containing element 3702 and the tissue and minimizing regions where the containing element 3702 is within a distance of the tissue that could be easily bridged by cured coating material 3704 prevent unwanted adhesion between the containing element 3702 and the tissue. This may be achieved through quick departure of the surface at least partial concavity of the containing element 3702 relative to the surface of the tissue near the contact sites 3710. A distal portion of the delivery system 3712, for example the containing element 3702, may be transparent to enable visualization of the cervix during application of the coating material. In some embodiments, a delivery system for delivery of an occlusive element and/or a coating material may contain at least one component that is translucent or transparent.

Figure 38:
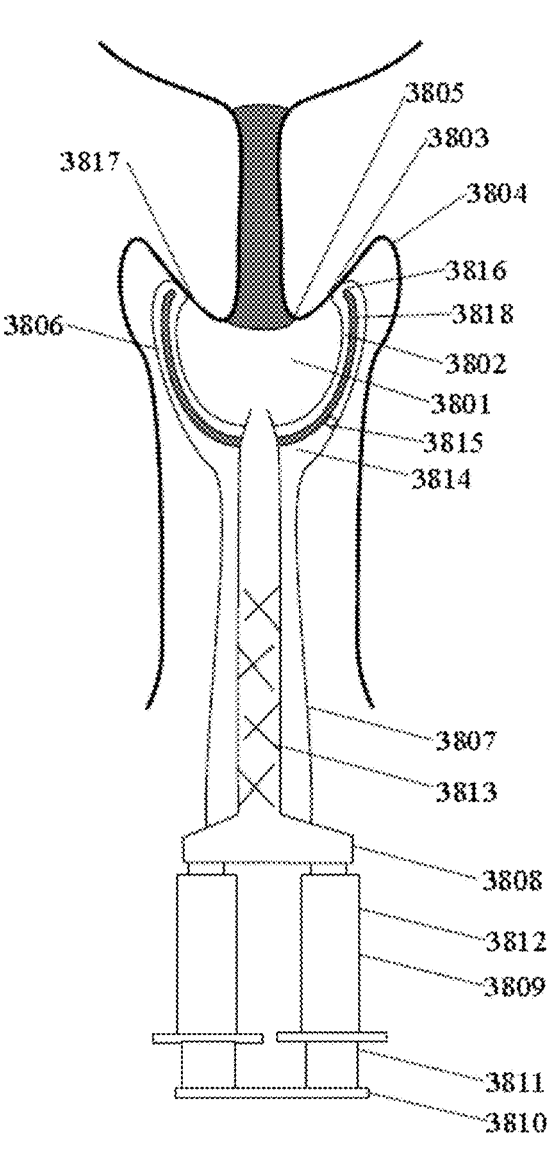
FIG. 38 illustrates another variation of an applicator apparatus for forming a microbial barrier on an ectocervix without disrupting the cervical mucus plug; in this variation the apparatus includes a plurality of chambers holding components of the coating material that may be mixed prior to application.

FIG. 38 depicts a delivery apparatus 3808 positioned near an ectocervix 3817 of a patient. In some embodiments, the delivery system 3808 may be introduced intravaginally and advanced until either a distal end of the delivery system 3816 is nested deep in the fornix 3804 or an interference fit is achieved with the ectocervix 3817. A volume 3801 may be isolated that is bounded at least in part by a peel-away containing element 3802 of a delivery system 3808 and the tissue intended for coating 3803. The volume is substantially filled with the coating material (not depicted), which is allowed to at least partially cure. The peel-away containing element 3802 is then peeled away from the cured coating material, beginning at edges of the cured coating material deeper into the fornix 3804 and progressing toward sites closer to the tip of the external os 3805; this is achieved by pulling on tensile structures 3806 coupled to the peel-away containing element 3802 at sites deeper into the fornix 3804, and also coupled to the elongate delivery member 3807 through which the coating material was injected. The tensile structures 3806 are coupled to the elongate delivery member in the first coupling region 3814 whereas the peel-away containing element 3802 is not coupled to the elongate delivery member 3807 or the tensile structures 3806 in the first coupling region 3814. The tensile structures 3806 are coupled to the peel-away containing element 3802 at the distal end of the delivery system 3816. The coating material may be formed from two components in syringes 3809 with a coupling element 3810 connecting the plungers 3811 to maintain a desired proportion of injected components. When the components of the coating material are ejected from the syringe barrels 3812, they may enter a conduit with mixing features 3813. In some embodiments, the coating material is pre-filled into the peel-away containing element 3802, rather than injected through the elongate delivery member 3807. In some embodiments, the tensile structures 3806 may help define or support a desired shape of the peel-away containing element 3802. They could be individual tensile members 3806, or they could be one cup-shaped structure (e.g., similar to one longitudinal half of an egg shell). In some embodiments, the delivery system 3808 features a port 3815 to prevent a vacuum in an internal region 3818, bordered by the peel-away containing element 3802 and a tensile member 3806, when peeling away the peel-away containing element 3802. In some embodiments, gaps may exist at an interface between the distal end of the delivery system 3816 and the tissue through which air can escape, or the fit at the interface may be loose enough for air to push through. In some embodiments, coating material exists from paths that go along a shape defining structure, through vacancies in an inner liner. In some embodiments, the delivery system 3808 contains a single syringe 3809, rather than more than one syringe. In some embodiments, the tensile structures 3806 may assist in defining a shape of the volume 3801 lined by the peel-away containing element 3802. A distal portion of the delivery system 3808, for example the containing element 3802, may be transparent or translucent to enable visualization of the cervix during application of the coating material.

In some cases, an obstetrician may assess the obstetric history of a pregnant woman during the first trimester of pregnancy and determine that the pregnant woman is of high risk of premature birth based on a history of prior premature birth. The obstetrician may make a determination to apply a coating material to the ectocervix of the pregnant woman between weeks 13 and 14 of pregnancy. This timing may be selected as vaginal bleeding is common during the first trimester of pregnancy, and it may be advantageous to apply the coating material after the period of time in which vaginal bleeding is common. Additionally, microbiota may ascend from the vagina to the uterus before 16 weeks of pregnancy, thus it may be advantageous to apply the coating material as early as feasible.

During an obstetric visit at week 13 of the pregnancy, the obstetrician may evaluate the pregnant woman for candidacy for application of the coating material. For example, the obstetrician may assess whether the pregnant woman's chorioamniotic membranes have ruptured and whether the pregnant woman has a reproductive tract infection. If the obstetrician finds that the pregnant woman's chorioamniotic membranes have not ruptured, and that the pregnant woman does not have a reproductive tract infection, the obstetrician may elect to proceed with the procedure.

For the procedure, the pregnant woman may be positioned as for a pelvic exam, in the dorsal lithotomy position with feet in stirrups. The obstetrician may insert a speculum into the vagina and visualize the cervix. The ectocervix may be prepared prior to application of the coating material. For example, the obstetrician may rinse the ectocervix with a saline spray, may apply an iodine solution to the ectocervix using a swab, and/or may gently apply a swab to remove mucus from target tissue. The coating material may be formulated to have durometer similar to that of the ectocervix during pregnancy. The obstetrician may use a delivery system for delivery of the coating material. The delivery system may comprise a double barrel syringe system containing components of the coating material, a mixing chamber, and an elongate delivery member. The obstetrician may introduce the elongate delivery member intravaginally under direct visualization and advance a semi-spherical locating feature at the distal end of the elongate delivery member towards the ectocervix. The locating feature may facilitate alignment of the delivery system with the ectocervix, and may be transparent to facilitate visualization. The obstetrician may advance the delivery system until the locating feature creates an interference fit with the ectocervix. The obstetrician may then visually confirm alignment of the delivery system and target tissue. The obstetrician may compress the double barrel syringe system, ejecting components of the coating material through the mixing chamber into a delivery lumen in the elongate delivery member, and out of spray ports into a volume defined by the ectocervix, cervical canal, and distal end of the elongate delivery member. A concave molding feature at the distal end of the elongate delivery member comprises a surface defining the volume and shaping the coating material. Air, excess coating material, and other substances can exit the volume through drain ports in the concave molding feature, and then flow through drain lumens in the elongate delivery member and exit the proximal end of the delivery system, out of the vagina. Once the volume has been filled with coating material, the obstetrician may cease compressing the double barrel syringe system and hold the delivery system in place for thirty seconds for the coating material to cure in a shape defined in part by the concave molding feature. The concave molding feature may facilitate applying coating material in a thickness between 1 mm and 1 cm. The obstetrician may then remove the delivery system and inspect the coating material to ensure that a barrier spanning the cervical canal has been applied. The coating material may contain a blue colorant to aid in assessment of the coverage of the coating material.

Following application of the coating material, the obstetrician may periodically re-apply coating material. For example, every four weeks until 34 weeks of gestation, the obstetrician may reassess the pregnant woman's candidacy for repeat application, including assessing the chorioamniotic membranes of the pregnant woman and assessing the pregnant woman for reproductive tract infection. If the obstetrician determines that the pregnant woman is a candidate for reapplication, the obstetrician may perform a procedure in which the coating material covering the pregnant woman's ectocervix is manually detached and removed, the ectocervix is prepared for reapplication, and coating material is applied to the ectocervix. In some cases, the coating material may comprise an occlusive element. In some cases, an initial application of the coating material may occur between weeks 1 and 37 of gestation, for example between weeks 8 and 20 of gestation.

Figure 39:
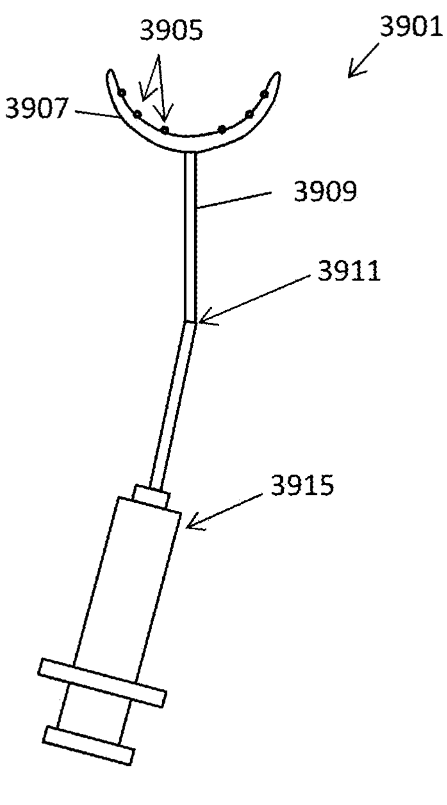
FIG. 39 illustrates one variation of a device for delivering a microbial barrier to an ectocervix of a cervix without disrupting a cervical mucus plug within a cervical canal.
Figure 40:
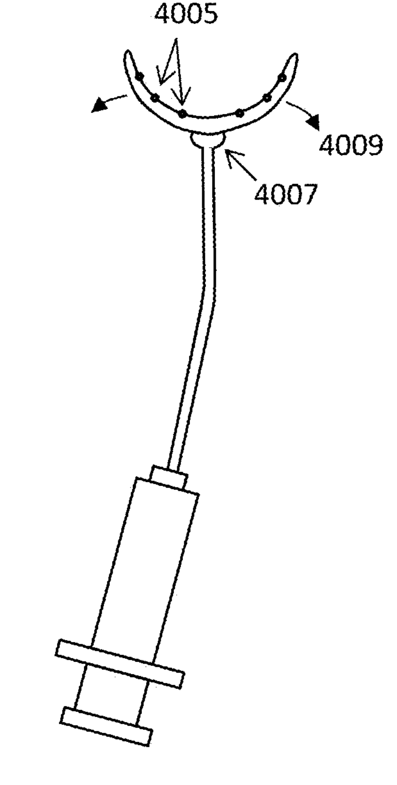
FIG. 40 illustrates another variation of a device for delivering a microbial barrier to an ectocervix of a cervix without disrupting a cervical mucus plug within a cervical canal.

FIGS. 39 and 40 illustrate examples of devices for delivering a microbial barrier to an ectocervix of a cervix without disrupting a cervical mucus plug within a cervical canal as described above. In FIG. 39, the apparatus includes a proximal end having a handle 3915 that incorporates a chamber (e.g., syringe) for holding the coating material. The chamber is connected by a delivery lumen (not visible) extending through the elongate body 3909. In this example, the elongate body is bent or bendable 3911 at a joint; the bend may be adjustable or fixed and adapted to allow the device to be positioned through the vagina so that the distal end (cup-shaped distal end 3907) may fit onto and/or opposite to the ectocervix. Thus, the apparatus may include an applicator 3907 at the distal end of the elongate body that is configured to be aligned over the ectocervix. The applicator may include an inner surface having a central region configured to be positioned opposite an opening into a cervical canal on the ectocervix when the applicator is aligned over the ectocervix (see FIGS. 41-43). The apparatus also includes one or more delivery apertures through the inner surface positioned outside of the central region, wherein the one or more delivery apertures are configured to deliver coating material from the first lumen to the ectocervix.

FIG. 40 is similar to the variation shown in FIG. 39, but also includes a bent or bendable neck region 4007 where the cup-shaped applicator attaches to the elongate body of the apparatus. This region may include a joint allowing the distal end region to bend.

Although the cup-shaped distal end region is shown in these examples as continuous, concave structures, in an of the apparatus variations described herein, the cup-shape may include gaps or openings, and/or may be formed by a plurality (e.g., 2 or more, 3 or more, 4 or more) arms or members forming the cup shape, from which the coating material may be applied. For example, three or more arms may extend radially out from the elongate member in a bent or curved shape, forming the cup shape.

Figure 41:
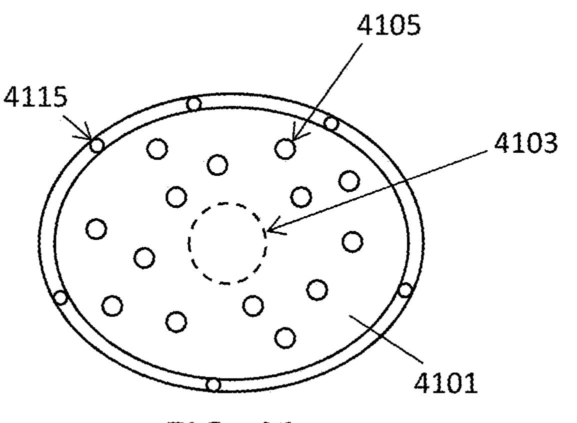
FIG. 41 shows one variation of the inner (concave) surface of the cup-shaped applicator at a distal end of a device for delivering a microbial barrier to an ectocervix of a cervix without disrupting a cervical mucus plug within a cervical canal.
Figure 43:
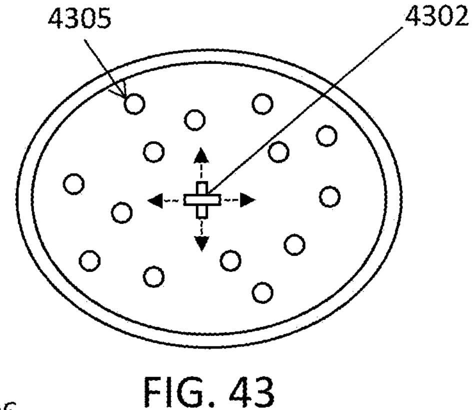
FIG. 43 is another variation of an inner surface of the cup-shaped applicator at a distal end of a device for delivering a microbial barrier to an ectocervix of a cervix without disrupting a cervical mucus plug within a cervical canal.
Figure 42:
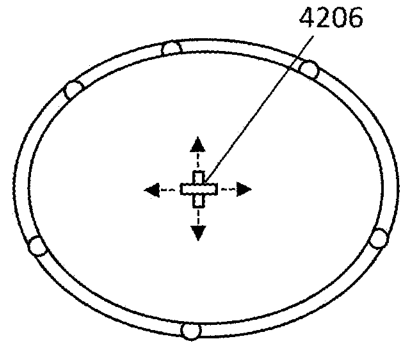
FIG. 42 is another variation of an inner surface of the cup-shaped applicator at a distal end of a device for delivering a microbial barrier to an ectocervix of a cervix without disrupting a cervical mucus plug within a cervical canal.

FIGS. 41-43 illustrate variations of the inner surface of a cup-shaped member. In FIG. 41, the inner surface includes a central region 4103 (dashed line) that is configured to be positioned opposite the cervical channel opening. In this example, this region is prevented from applying coating material directly into the channel opening and does not includes any apertures 4105 as shown elsewhere (radially offset) on the inner surface. In this example, the cup-shaped applicator is oval, rather than circular, which may more accurately conform to the shape of the ectocervix; alternatively the cup-shape may be circular or may have other cross-sectional shapes.

The outer perimeter of the cup-shaped applicator shown in FIGS. 41 and 42 includes plurality of return ports (openings, apertures, etc.) that may be connected to an overflow channel(s); these return/overflow ports are positioned at the periphery of the inner surface in this example though they may be positioned more radially inward, including near the central region.

FIG. 42 illustrates an example of an inner surface including a delivery aperture 4206 for applying coating material that is positioned within the central region 4103 of the inner surface but that is oriented to prevent emitting coating material perpendicular to the central region and into the cervical canal when the cup-shaped applicator is over the ectocervix. In this variation, four apertures (or a single aperture having four oriented exits) is/are positioned in the central region with openings that direct and/or deflect the coating material in a direction that is normal to (+/−45 degrees, +/−30 degrees, +/−25 degrees, +/−20 degrees, +/−15 degrees, etc.) the face of the cervical opening when the applicator is positioned over the cervix. In this way, the apparatus may protect the cervical opening and canal from having coating material delivered/forced into the canal, and thereby disrupting/dislodging the cervical mucus plug.

FIG. 43 illustrates another variation of the inner surface of a cup-shaped applicator that includes both delivery apertures 4305 through the inner surface, wherein the delivery apertures are outside of the central region and one or more apertures 4302 oriented to prevent emitting coating material perpendicular to the central region and into the cervical canal when the cup-shaped applicator is over the ectocervix.

Also described herein are methods and devices for the transfer of human microbiota and/or human-derived microbiota to the female reproductive system of a patient. In some embodiments, microbiota is collected from the female reproductive system of a pre-screened donor, and then is transplanted to the female reproductive system of a selected recipient. In some embodiments, microbiota collected from a pre-screened donor is processed to yield human-derived microbiota, and then the human-derived microbiota is transferred to the female reproductive system of a selected recipient. Any of the methods for transferring human microbiota may be used alternatively or additionally with the apparatuses and methods for forming a microbial barrier described above.

Screening of Prospective Donors

Prospective donors may be screened before donation of donor material, after donation of donor material, or both before and after. The following criteria are examples of criteria that may be used in screening to exclude a prospective donor: recent antibiotic exposure, for example, in the past six months; being immunocompromised; history of autoimmune illness; ongoing immune modulation therapy; ongoing oncologic therapy; chronic disorders of the female reproductive tract, for example recurrent bacterial vaginosis; prior adverse pregnancy outcomes, for example having an infection-mediated preterm birth; history of sexually transmitted disease; history of high-risk sexual practices; history of illicit drug use; known current communicable disease; metabolic conditions, for example BMI>30.

The serum of a prospective donor may be tested, for example to ensure that the prospective donor does not have HIV, Hepatitis A, Hepatitis B, Hepatitis C, or syphilis.

The microbiota of a prospective donor's female reproductive system may be analyzed, for example to determine whether the microbiota meets a predetermined standard. In another example, the analysis may be undertaken to exclude prospective donors with *C. difficile*. Microbiota samples for analysis may be taken from one or more locations within a prospective donor's female reproductive system.

Collection of Donor Material

Donor material comprises material that contains microbes and is collected from the female reproductive system and/or gestational tissue and/or fetal tissue and/or fetal fluids. Non-limiting examples of donor material include cervical mucus, vaginal secretions, vaginal discharge, amniotic fluid, placenta, and chorioamniotic membranes. Non-limiting examples of techniques to collect donor material include aspiration and swabbing.

A region of the female reproductive system may be prepared prior to the collection of donor material. For example, the cervix may be washed in sterile saline prior to collection of cervical mucus.

Processing of Donor Material

Prior to transplantation to a recipient, donor material may be processed. In some cases, donor material may be combined with another material such as a diluting agent. For example, donor material may be combined with saline solution. Said materials may be mixed in a blender.

In some cases, donor material may be stored in a freezer or refrigerator prior to transplantation. For example, donor material may be stored in a freezer at temperatures between −10 degrees Celsius and −100 degrees Celsius, such as at −75 degrees Celsius. In some cases, an additive such as glycerol may be combined with donor material prior to refrigeration or freezing.

In some cases, processing may also include sieving donor material with a strainer, centrifuging donor materials, and/or separating donor material based on particle size and/or density.

In some cases, multiple samples of donor material, such as samples collected from a single donor over a period of time, or such as samples collected from more than one donor, may be combined. For example, said combination may be utilized to achieve a target volume of donor material for transplantation.

In some cases, human-derived microbiota comprises microbiota derived from a sample collected from a donor's female reproductive system; in some cases human-derived microbiota comprises microbiota from a sample collected from a region of a donor other than the female reproductive system. In some cases, bacteria from a sample collected from a donor may be isolated by culture. The cultured bacterial strains may be tested for susceptibility to antimicrobials, and any cultured bacterial strain with poor susceptibility may be excluded from inclusion in the human-derived microbiota product. One or more of the cultured bacterial strains with acceptable antimicrobial susceptibility may be selected as a constituent of the human-derived microbiota. If more than one cultured bacterial strain was selected, the cultured bacterial strains may be combined at a predetermined ratio to produce the human-derived microbiota. An additive such as saline solution may be combined with the human-derived microbiota at a predetermined ratio.

In some cases, human-derived microbiota comprises a mixture of between two cultured bacterial strains and one thousand cultured bacterial strains, for example fifteen cultured bacterial strains, to be administered concurrently. In some cases, human-derived microbiota comprises a mixture of bacterial species that includes species from two or more phyla.

Therapeutic Objective

Non-limiting examples of therapeutic objectives include improvement of an outcome associated with in vitro fertilization, such as improvement of the likelihood of implantation, and/or clinical pregnancy, and/or live birth; improvement of an outcome associated with pregnancy, such as improvement of the likelihood of term birth and/or to decrease the likelihood of preterm birth, and/or early preterm birth, and/or infection-mediated preterm birth, and/or microbiota-related preterm birth, and/or preterm premature rupture of membranes; improvement of an outcome associated with the female reproductive health system, such as resolution of recurrent bacterial vaginosis and/or chronic endometritis.

Selection of Prospective Recipients

Prospective recipients may be screened for qualification to receive a microbiota transfer. For example, a patient's obstetric history may be analyzed as part of the screening process; prior infection-mediated early preterm pregnancy may be used as component of inclusion criteria for patient selection. Other factors that may be used as a component of inclusion criteria include poor outcome in a prior in vitro fertilization attempt (for example, implantation failure in conjunction with recovery of *Streptococcus viridans* from the embryo transfer catheter tip) and/or infection of a component of the female reproductive system, such as recurrent bacterial vaginosis. Microbiota of a potential target location in the patient's female reproductive system may be assessed. The screening may include analysis of prospective recipient's female reproductive system microbiota, for example by culture based methods and/or by molecular methods such as polymerase chain reaction assays. Determination that the microbiota is unfavorable based on a predetermined standard and/or determination that the microbiota is amenable to microbiota transfer treatment based on a predetermined standard may be prerequisite for selection of the prospective recipient as a qualified recipient. Screening may include genetic screening of a prospective recipient, for example to assess factors associated with the prospective patient's risk of microbiota-related preterm birth. Prospective patients with neutropenia may be excluded as qualified patients.

Recipient Material

Recipient material comprises human microbiota and/or human-derived microbiota and/or microbiotic material and/or a growth promoting agent and/or an agent for promoting the growth of a subset of microbiota and/or a growth retarding agent and/or an agent for retarding the growth of a subset of microbiota and/or material for promoting a desired microbiotic profile. Recipient material may also contain a dilutant such as saline solution and/or an additive such as glycerol. Non-limiting examples of recipient material include donor material and human-derived microbiota, such as human-derived microbiota processed from a sample from the female reproductive system of a donor as described above.

Timing of Delivery to Recipient

In some cases, recipient material may be administered to a recipient prior to an intended pregnancy, and/or during a pregnancy, and/or following a pregnancy.

In some cases, recipient material may be administered to a recipient prior to, and/or current with, and/or following an in vitro fertilization procedure.

In some cases, recipient material may be administered to a recipient following diagnosis of a condition affecting the female reproductive system.

In some cases, delivery of recipient material to a patient may be repeated over the course of two or more sessions.

Delivery of Microbiota to Recipient

Delivery of recipient material may be targeted to specific region(s) within a patient's female reproductive system. Non-limiting examples of targets include regions of the vagina, cervix, and uterus. Additionally, recipient material may be delivered to a location from which the microbiota are known or believed to have a high likelihood of spreading to the female reproductive system. For example, recipient material may be administered orally or inserted in the gastrointestinal tract of a patient.

Recipient material may be intended to remain in the patient's body for a range of times. For example, the bulk of recipient material inserted into a patient's vagina may be intended to remain in the patient's vagina for at least six hours. More generally, the bulk of recipient material may be intended to remain in the patient's body for between 1 second and 1 week. The patient may be oriented in order to minimize likelihood of prematurely evacuating recipient material; for example, the patient may lie horizontally on her back during the course of a treatment session. In some cases, a device may be employed to prevent or reduce premature evacuation of recipient material. For example, a tampon-like device may be inserted into a patient's vagina prevent or reduce premature evacuation of recipient material from the vagina.

In some cases, tissues near the vagina, the vagina, the cervical canal, and/or the uterus are partly or fully cleared of pre-existing microbiota, ahead of delivery of new microbiota.

Recipient material may be formulated to prevent or reduce premature evacuation of recipient material from a patient's body. Recipient material may be formulated as a gel; and/or may be formulated as a non-Newtonian fluid, for example as a Bingham plastic; and/or may have a high viscosity. Recipient material may be formulated as a fluid or gel, and may have a viscosity that varies over time; for example, recipient material may change from a higher viscosity to a lower viscosity over an 8 hour period following an activation procedure. Recipient material may comprise a pill with a soluble outer layer and an inner core comprising microbiota, such as human microbiota and/or human-derived microbiota. For example, said pill may be placed in a patient's vagina where the outer layer dissolves, exposing the microbiota in the inner core. Recipient material may be embodied as a structure that gradually delivers microbiota, such as human microbiota and/or human-derived microbiota, over a period of time. For example, recipient material may be embodied as a pill containing a matrix that gradually delivers microbiota over the course of one week. Recipient material may be formulated as a suppository.

In some embodiments and methods, a system for delivery of fluid recipient material and/or gel recipient material may contain means for limiting the flow rate, and/or means for limiting the pressure with which recipient material is delivered to a patient. For example, a pressure relief valve in fluid communication with a delivery lumen of a delivery catheter may limit pressure of recipient material delivered to a patient to a preset threshold. In another example, an infusion pump may be utilized to control the flow rate of recipient material delivered to the patient. The infusion pump may be purely mechanical, with a compressed spring providing a known range of forces, and a length of tubing providing a known rage of resistance. In other embodiments and methods, the infusion pump may contain electrical components. The system may include a feature for minimization of turbulence of recipient material in the system and/or for minimization of turbulence of recipient material in a lumen of the patient.

In some cases, a delivery port positioned within the vagina, cervical canal, or uterus may be configured or used to deliver material as the delivery port is withdrawn, or moved in a withdrawing direction, from the vagina, in order to prevent delivered recipient material from pushing deeper into the vagina previously delivered recipient material and/or pre-existing matter within the birth canal.

In some cases, an occluding element may be positioned at a first vaginal, cervical, or uterine location. The occluding element (for example, an inflatable balloon, a region augmented diameter on a delivery device, or a region containing negative pressure ports that promote apposition of the delivery device to surrounding tissues) is activated if necessary prior to the delivery of recipient material into the vagina, cervical canal, and/or uterine location. The occluding element may be positioned distally to (e.g., deeper in the vagina, cervical canal, or uterus) the location at which the recipient material is delivered; for example a delivery catheter may contain a distal occluding element and a delivery port proximal to the occluding element. The occluding element prevents some or all of the delivered recipient material from reaching sites deeper in the vagina, cervical canal, or uterus than the occluding element during delivery, and/or prevents delivery from pushing native microorganisms deeper in the vagina, cervical canal, or uterus. In some cases, delivery of the recipient material is stopped when injected material reaches the vaginal opening. In some cases, the delivery device is low-profile, as to prevent pushing material in the vagina to a deeper location during device insertion.

In some embodiments and methods, a catheter for delivery of recipient material may comprise a fluid delivery lumen extending from an fluid delivery ostium at or near the distal tip of the catheter to a proximal reservoir of recipient material, and further comprising a vent lumen extending a vent intake ostium at or near the distal tip of the catheter to an outflow reservoir near the proximal end of the catheter. The outflow reservoir may comprise a non-sealed container that vents to the surrounding air. The catheter's tip may be inserted in a patient's vagina, recipient material may be caused to flow from the reservoir through the fluid delivery lumen, and exit the fluid delivery ostium. Air and/or fluid in the vagina, including air and/or fluid that was in the vagina immediately prior to the insertion of the catheter, may enter the vent intake ostium and flow through the vent lumen. The flow of air and/or fluid through the vent lumen to the outflow reservoir may prevent or minimize an increase in pressure in the vagina as the catheter is inserted and/or as recipient material is delivered.

In some cases, delivery devices are configured and used in manner such that the volume of delivered material at the delivery site approximately replaces the volume evacuated by the delivery device during delivery, to minimize or avoid pressure differentials that may cause unwanted migration of the delivered material and/or native microorganisms.

In some cases, a delivery device is inserted into the vagina, cervical canal, or uterus, and features a plunger that, when activated, causes material to exit through ports. In some cases, the sizes, resistances, and locations of the ports are chosen to promote a desired distribution of delivered material within the target anatomy. For example, the ports may be configured such that delivered material is positioned approximately evenly within a target region (for example, by preventing any subset of ports from being isolated from the contained material during activation of the plunger, or by using port sizes, resistances, and locations that accommodate for such isolation). In some cases, materials are delivered in amounts and/or proportions that vary along or around the device, in order to promote a desired microbiota profile. For example, microbiotic material with a desired microbiotic profile may be delivered at a first region nearer the vaginal opening than a second region, where a growth retarding agent may be delivered (or a growth retarding agent delivery device, or a plugging or blocking device, delivered).

In some cases, a plugging or blocking device may be implanted in a vaginal, cervical canal, and/or uterus to prevent ascension or migration of microorganisms. The plugging or blocking device may be biodegradable.

In some embodiments and methods, recipient material may be delivered a system comprising a fluid reservoir connected to a flexible tube with an atraumatic tip. The flexible tube may contain a valve that can be turned to block flow, or to allow flow depending on the operator's preference. In some cases, the system may be powered by gravity, wherein the fluid reservoir containing recipient material is elevated relative to the tip of the flexible tube, and the tip of the flexible tube is inserted near a target location of the patient. In some cases, flow of recipient material in the system may be powered by pump.

In some embodiments and methods, a syringe containing recipient material may be coupled to a delivery catheter. The delivery catheter may contain a fluid delivery port on the distal tip, connected via a fluid delivery lumen to the syringe. The distal tip may be inserted by an operator in a patient's vagina, and advanced to a target location. After aligning the fluid delivery port with the target location, the operator may advance a plunger of the syringe, thereby delivering recipient material to the target location. In some cases, a guide catheter is used in conjunction with a delivery catheter. The delivery catheter may have a more flexible shaft than the guide catheter.

In some embodiments and methods, recipient material may be delivered from a hysteroscope, for example, via a working port. In some embodiments and methods, recipient material may be delivered from an embryo transfer catheter.

A delivery catheter or other recipient material delivery device may comprise one or more of the following: a soft distal tip, a bulb shaped tip, a flexible shaft, an echogenic tip, an echogenic shaft, a feature to mechanically prevent over-insertion, and markings along a shaft to facilitate determination of insertion depth.

Delivery of microbiota to the recipient may be conducted with imaging, for example, transcutaneous ultrasound, and/or fiber optic visualization. In some embodiments and methods, direct visualization may be employed, for example in conjunction with a speculum.

In some cases, the recipient material is prefilled in a delivery device before the device is positioned in the anatomy. For example, a delivery device may be prefilled with human-derived microbiota.

In some cases, the amount or microbiotic profile of recipient material delivered is chosen at least in part based on characteristics of a recipient, such as the native microbiotic profile. For example, bacterial strains and/or a ratio of bacterial strains may be selected based on analysis of the recipient's vaginal microbiota, and/or based on the patient's genome, and/or based on the patient's clinical presentation. In another example, recipient material with a relatively high proportion of a particular desired microorganism may be delivered to a patient with an undesirably low natural proportion of the microorganism in a native microbiota.

In some cases, the microbiotic profile of material delivered to a patient may vary between administrations.

In some cases, a first device that resides in the vagina, cervical canal, or uterus for an extended period (for example, a period lasting long enough for measurable changes in the microbiotic profile to occur) senses conditions (for example, pH, dryness, or temperature) or changes in conditions. In some cases, this information is stored within the first device, then transmitted to a second device (for example, a smartphone), and in some cases, additional devices in sequence or parallel. In some cases, the first device, second device, or additional devices provide visual, audible, or tactile information to a person (for example, the wearer of the first device, or a medical professional) that can be used to determine whether to take a course of action (for example, to deliver microbiotic material to the body). In some cases, a delivering device (for example, the first device) may, in response to sensed conditions or changes in conditions, deliver a material or treatment to the body, in order to promote a desired microbiotic profile. For example, a delivering device may deliver one or more of: recipient material, and/or the delivering device may deliver light, buffering solution (or other solutions intended to affect pH), cold therapy, heat therapy, or another therapy.

In some cases, a device remains in place in the vagina, cervical canal, and/or uterus, and promotes a desired microbiotic profile. For example, the device may expose the microbiota to metal ions believed or known to promote the proliferation of particular bacteria. For example, manganese or ferrous ions may be present to promote the growth of *Lactobacillus*. In some cases, recipient material may be released gradually from the device. In some cases, microorganisms may be released in proportions that differ from the proportion present in the vagina, cervical canal, and/or uterus, in order to change the microbiotic profiled to a desired state.

In some cases, devices or methods of promoting a desired microbiome profile involve providing light at a wavelength, duration, intensity, and/or regimen that promotes desired growth or inhibition of growth of microorganisms, or one or more subsets of microorganisms present in a microbiota. The parameters of light delivery may be chosen to prevent unwanted damage or risk of damage to tissues, for example due to ultraviolet light exposure and/or heat.

In some cases, a reservoir of material, such as recipient material, may reside outside of the primary site of the target microbiota, until it is delivered to the primary site of the microbiota according to a desire protocol. In some cases, the reservoir of material is adhered to the skin or secured to a garment, and a conduit runs from the reservoir to the primary site of the microbiota. For example, a reservoir may be adhered to the thigh, and a microcontroller may regulate the pumping or release of a microbiotic fluid through a tube into the vagina. In some cases, the reservoir system functions similarly to an insulin pump.

In some cases, devices or methods of promoting a desired microbiome profile involve maintaining a desired pH at the site of the microbiota, for example, a pH known or believed to promote the relative growth of a microorganism whose prevalence or abundance is lower than desired, or in another example, a pH known or believed to inhibit the relative growth of a microorganism whose prevalence or abundance is higher than desired. For example, a pH may be promoted that is conducive to the growth of *Lactobacillus*. In some cases, a device facilitates the immediate release or gradual release of an agent (for example, a buffering agent) that affect the pH of the microbiota's environment.

In some cases, the devices and methods described herein may be used to transplant or deliver recipient material to eyes, ears, urinary tracts, gastrointestinal tracts, oral cavities, reproductive systems, and/or respiratory systems of recipients. In some cases, the materials originate in the corresponding anatomy of donors.

It should be understood that the term "microbiota," as used in this application, may refer to a collection or subcollection of microorganisms found on or within a larger organism, and/or to a collection or subcollection of microorganisms that is desired to be placed, cultivated, or promoted on or within a larger organism. It should be understood that the term "microbiotic profile" may refer to the composition, relative composition, and/or amount of microorganisms present in a microbiota.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A medical device, comprising:

a device configured to assume a volume fully within a female reproductive tract, fully outside of a uterine cavity, between a first region of the female reproductive tract and a second region of the female reproductive tract, and at least partially surrounding a vaginal portion of a cervix;

wherein the device is configured to occupy at least part of a path from a first site in a vagina of the female reproductive tract to a second site on the cervix, in a cervical canal of the cervix, or in the uterine cavity of the female reproductive tract;

wherein the device includes a contacting region that is configured to impart a normal force that is in a direction perpendicular to and against a vaginal wall and/or a frictional force on the vaginal wall, from which results an opposing force that is opposite the normal force and/or an opposing frictional force that favors a stable position of the device;

wherein the device is configured to provide at least one unobstructed path from the second site to the first site;

wherein the device is configured to isolate the first region of the female reproductive tract from the second region of the female reproductive tract; and wherein the first region is a region where a type, proportion, quantity, distribution, or proliferation of a microorganism is suspected to be or to become present, and wherein the second region is a region where the type, proportion, quantity, distribution, or proliferation of the microorganism is unwanted.

2. The medical device of claim 1, further comprising one or more of: an antimicrobial agent; a drug; an antibacterial agent; a material or a combination of materials having antibacterial properties; a material that possesses antimicrobial properties; a coating comprised of an agent that affects bacterial growth.

3. The medical device of claim 1, further comprising a light-emitting component configured to deliver an antimicrobial light onto a path between the first site and the second site.

4. The medical device of claim 1, further comprising a handling feature.

5. The medical device of claim 1, wherein the device is configured to include one or more tissue-contacting augmentations configured to impart the normal force and/or the frictional force on the vaginal wall.

6. The medical device of claim 1, the device is configured to provide at least one continuous path from the second site to the first site along a surface of the device.

7. The medical device of claim 1, wherein the device is configured to increase a length of a shortest unobstructed path between the second site and the first site.

8. The medical device of claim 1, wherein the device is configured to increase an unobstructed distance between the second site and the first site.

9. The medical device of claim 1, wherein the device is configured to cover an external opening of the cervical canal of the cervix.

10. The medical device of claim 1, wherein the device is configured to prevent disruption or dislodging of a cervical mucus plug formed during pregnancy.

11. A medical device, comprising:

a device configured to assume a volume fully within a female reproductive tract, fully outside of a uterine cavity, and between a first region of the female reproductive tract and a second region of the female reproductive tract;

wherein the device is configured to occupy at least part of a path from a first site in a vagina of the female reproductive tract to a second site on a cervix, in a cervical canal of the cervix, or in the uterine cavity of the female reproductive tract;

wherein the device includes a contacting region that is configured to impart a normal force that is in a direction perpendicular to and against a wall of the female reproductive tract and/or a frictional force on the wall, from which results an opposing force that is opposite the normal force and/or an opposing frictional force that favors a stable position of the device;

wherein the device is configured to provide at least one unobstructed path from the second site to the first site; and wherein the first region is a region where a first type, proportion, quantity, distribution, or proliferation of a microorganism is suspected to be or to become present, and wherein the second region is a region where the first type, proportion, quantity, distribution, or proliferation of the microorganism is unwanted.

12. The medical device of claim 11, configured to assume a volume at least partially surrounding a vaginal portion of the cervix, and wherein the wall is a vaginal wall of the female reproductive tract.

13. The medical device of claim 11, configured to assume a volume at least partially within the cervical canal of the female reproductive tract, and wherein the wall is a wall of the cervical canal of the female reproductive tract.

14. The medical device of claim 11, further comprising one or more of: an antimicrobial agent; a drug; an antibacterial agent; a material or a combination of materials having antibacterial properties; a material that possesses antimicrobial properties; a coating comprised of an agent that affects bacterial growth.

15. The medical device of claim 11, further comprising a light-emitting component configured to deliver an antimicrobial light onto a path between the first site and the second site.

16. The medical device of claim 11, wherein the device is configured to prevent disruption or dislodging of a cervical mucus plug formed during pregnancy.

17. A method of reducing risk of premature birth in a patient, comprising:

(a) receiving a device configured to:
   (i) assume a volume fully within a female reproductive tract, fully outside of a uterine cavity, between a first region of the female reproductive tract and a second region of the female reproductive tract, and at least partially surrounding a vaginal portion of a cervix;
   (ii) occupy at least part of a path from a first site in a vagina of the female reproductive tract to a second site on the cervix, in a cervical canal of the cervix, or in the uterine cavity of the female reproductive tract;
   (iii) include a contacting region configured to impart a normal force perpendicular to and against a vaginal wall and/or a frictional force on the vaginal wall, from which results an opposing force opposite the normal force and/or an opposing frictional force that favors a stable position of the device;
   (iv) provide at least one unobstructed path from the second site to the first site; and
   (v) isolate the first region of the female reproductive tract from the second region of the female reproductive tract, wherein the first region is a region where a type, proportion, quantity, distribution, or proliferation of a microorganism is suspected to be or to become present, and wherein the second region is a region where the type, proportion, quantity, distribution, or proliferation of the microorganism is unwanted;

(b) positioning the device in the female reproductive tract of the patient, thereby reducing risk of premature birth in the patient.

18. The method of claim 17, further comprising screening the patient for candidacy for the method, the screening comprising:

(a) assessing at least one criterion selected from a group consisting of:
   (i) having previously given birth prematurely;
   (ii) previous miscarriage;
   (iii) positive or negative test for a particular type, proportion, quantity, distribution, and/or proliferation of microorganisms in a female reproductive system of the patient;
   (iv) elevated risk of premature birth, according to known and/or suspected risk factors;
   (v) cervical insufficiency;
   (vi) prior cervical surgery;
   (vii) removal of at least a portion of a cervical gland;
   (viii) having a reproductive tract infection;
   (ix) having bacterial vaginosis;
   (x) having intermediate bacterial flora as assessed based on a Nugent score;
   (xi) elevated vaginal pH;
   (xii) having an elevated level of sialidase in at least a part of the female reproductive system of the patient;
   (xiii) elevated cervical mucus permeability;
   (xiv) elevated cervical mucus spinnbarkeit;
   (xv) low cervical mucus viscosity; and (b) selecting the patient for the method when the at least one criterion is met.

19. The method of claim 17, further comprising screening the patient for candidacy for the method, the screening comprising:

(a) evaluating at least one characteristic of a cervical mucus plug selected from a group consisting of:
   (i) length;
   (ii) permeability;

(iii) impedence;
(iv) modulus of elasticity;
(v) spinnbarkeit;
(vi) storage modulus;
(vii) loss modulus;
(viii) transparency;
(ix) color; and (b) selecting the patient for the method based on the evaluation.

20. The method of claim 17, wherein the device is configured to isolate a lower vaginal region of the female reproductive tract from a region of the cervical canal of the cervix.

* * * * *